(12) United States Patent (10) Patent No.: US 12,635,859 B2

Sigmon, Jr. et al. (45) Date of Patent: May 26, 2026

(54) ENDOSCOPE WITH KEYED ORIENTATION FEATURE

(71) Applicant: Cook Medical Technologies LLC, Bloomington, IN (US)

(72) Inventors: John C. Sigmon, Jr., Winston-Salem, NC (US); Shaun D. Gittard, Winston-Salem, NC (US); Liam Breen, Ballina (IE); Vincent McHugo, Birdhill (IE); Jonathan Lupton, Thomasville, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 491 days.

(21) Appl. No.: 18/155,250

(22) Filed: Jan. 17, 2023

(65) Prior Publication Data

US 2023/0233065 A1 Jul. 27, 2023

Related U.S. Application Data

(60) Provisional application No. 63/303,677, filed on Jan. 27, 2022.

(51) Int. Cl.
*A61B 1/00* (2006.01)
*A61B 1/018* (2006.01)

(52) U.S. Cl.
CPC ........ *A61B 1/00148* (2022.02); *A61B 1/0014* (2013.01); *A61B 1/018* (2013.01)

(58) Field of Classification Search
CPC ... A61B 1/00148; A61B 1/0014; A61B 1/018; A61B 1/00135; A61B 1/00142; A61B 1/00073
See application file for complete search history.

(56) References Cited

U.S. PATENT DOCUMENTS 6,203,493 B1 * 3/2001 Ben-Haim ............. A61B 5/065
600/117
7,918,783 B2 4/2011 Maseda et al.
(Continued)

FOREIGN PATENT DOCUMENTS

EP 1284120 A1 2/2003
WO WO 2010/135325 A1 11/2010
(Continued)

OTHER PUBLICATIONS

International Search Report and Written Opinion in International Application No. PCT/US2023/060733, dated May 4, 2023, 14 pages.
(Continued)

*Primary Examiner* — Timothy J Neal

(74) *Attorney, Agent, or Firm* — Vivacqua Crane, PLLC

(57) ABSTRACT

Disclosed herein is a medical device including a camera including a movable member including an outer surface with a longitudinally-extending cross-sectional geometry configured to complement a longitudinally-extending cross-sectional geometry of a surface of a lumen in an elongate tube housing the movable member so as to prevent rotation of the movable member relative to the elongate tube. The device allows the operator to maintain visual orientation as the movable member is translated proximally and distally relative to the elongate tube.

15 Claims, 14 Drawing Sheets

(56)  References Cited

U.S. PATENT DOCUMENTS

| | | | |
|---|---|---|---|
| 8,007,440 B2 | 8/2011 | Magnin et al. | |
| 8,190,238 B2 | 5/2012 | Moll et al. | |
| 8,391,957 B2 | 3/2013 | Carlson et al. | |
| 8,852,084 B2 | 10/2014 | Crank | |
| 9,931,026 B2 | 4/2018 | Ha et al. | |
| 10,478,052 B2 | 11/2019 | Konstorum et al. | |
| 10,582,837 B2 | 3/2020 | Hebert | |
| 10,588,597 B2 | 3/2020 | Zhao et al. | |
| 2005/0277808 A1* | 12/2005 | Sonnenschein | A61B 1/053 |
| | | | 600/153 |
| 2007/0112250 A1* | 5/2007 | Kura | A61B 1/31 |
| | | | 600/156 |
| 2007/0244356 A1 | 10/2007 | Carrillo, Jr. et al. | |
| 2009/0259103 A1 | 10/2009 | Hirata | |
| 2014/0114126 A1* | 4/2014 | Dresher | A61B 1/0125 |
| | | | 600/106 |
| 2018/0055334 A1* | 3/2018 | Ando | A61B 1/00112 |
| 2018/0296073 A1 | 10/2018 | Dejima et al. | |
| 2019/0209154 A1 | 7/2019 | Richter et al. | |
| 2020/0323424 A1 | 10/2020 | Hazelton et al. | |
| 2021/0000333 A1 | 1/2021 | Sakai et al. | |
| 2021/0100627 A1 | 4/2021 | Soper et al. | |

FOREIGN PATENT DOCUMENTS

| | | |
|---|---|---|
| WO | 2017119401 | 7/2017 |
| WO | 2019181042 | 9/2019 |

OTHER PUBLICATIONS

Japanese Patent Office. Office Action for JP Application No. 2024-544682 and English translation, mailed Jul. 1, 2025, pp. 1-10.

* cited by examiner

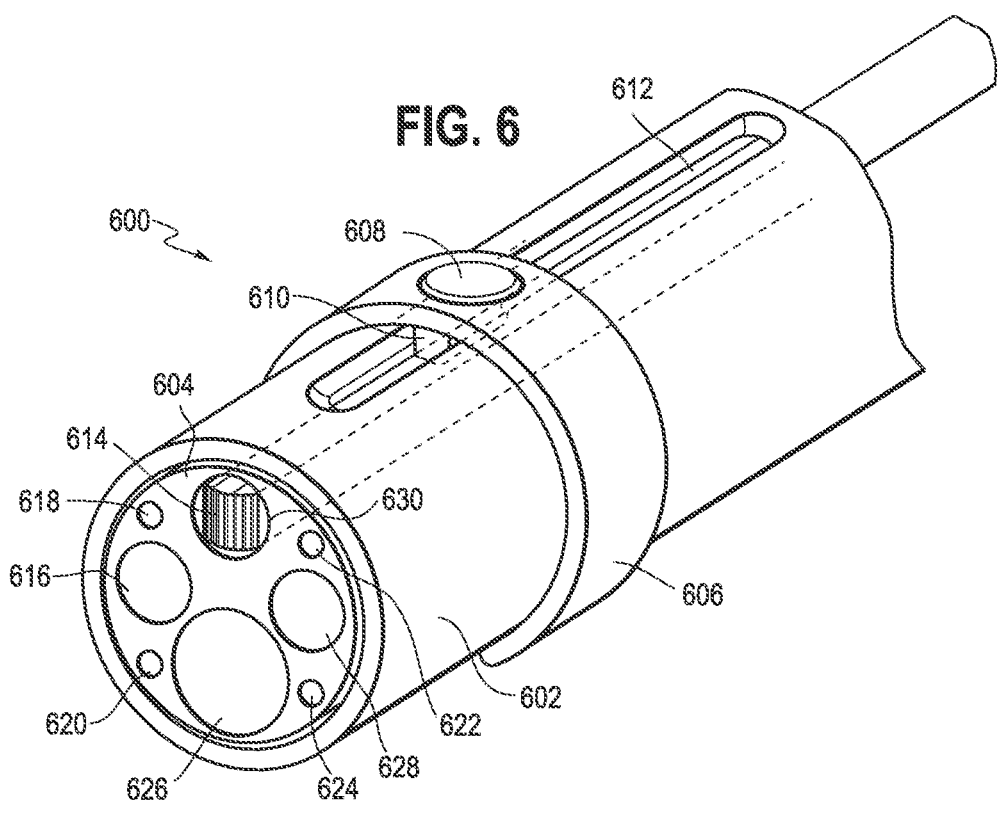
FIG. 6
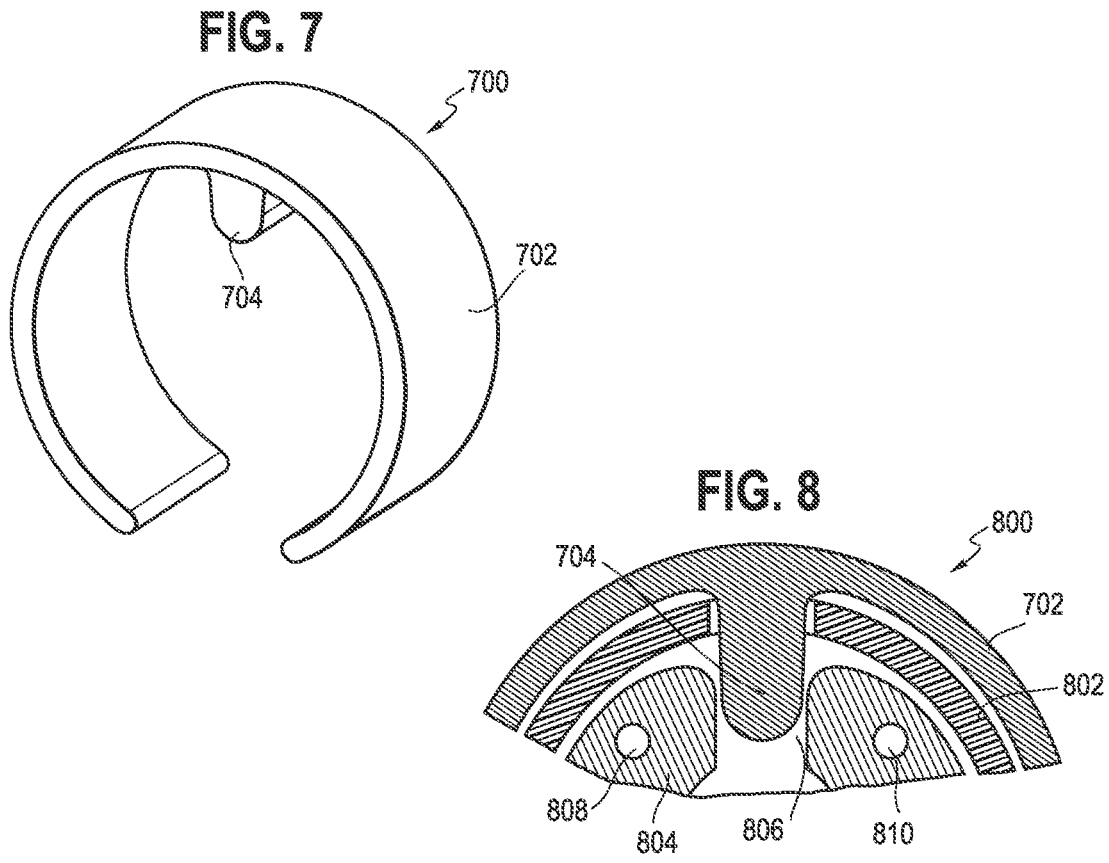
FIG. 7
FIG. 8

Section View A-A

Section View B-B

Distal

View

Side View

Section C-C

Distal

View

Side View

ENDOSCOPE WITH KEYED ORIENTATION FEATURE

CROSS-REFERENCE TO RELATED APPLICATIONS

The present application claims the benefit of U.S. Provisional Application No. 63/303,677, filed Jan. 27, 2022, which is incorporated by reference herein in its entirety for all purposes.

FIELD

The present disclosure relates to medical devices. More particularly, the disclosure relates to features for maintaining orientation of telescoping cameras in endoscope systems.

BACKGROUND

The statements in this section merely provide background information related to the present disclosure and may not constitute prior art.

Internal body cavities and body lumens may become blocked, or the walls surrounding them may develop growths. In some cases, removal of these blockages or growths, or other treatment thereof, may be necessary. Endoscopic or other minimally invasive techniques may be used to treat these situations.

One type of treatment includes the use of catheters or other endoscopic devices that are inserted into the body lumen or cavity and toward the area where treatment is desired. Insertion of the endoscope to the target area can allow for visualization of the target area and a determination of the desired procedure and the specific location of the area to be treated.

In general, endoscopes have been designed to be operated with the same fundamental mechanisms, and have not had transformational improvements. Endoscopes generally include a camera and a set of wheels that an operator, such as a physician, operates with a first hand (in some cases, the left hand) to control scope deflection, while the second (generally, right) hand switches between the insertion tube of the endoscope and the accessory channel in order to control scope and device advancement, respectively, through the anatomy of a patient.

Specialized endoscopes, tailored to specific procedures, are becoming more common in the field of endoscopy with the trend from reusable scopes to disposable scopes. The camera of some specialized endoscopes may be extended or telescoped out of the endoscope body or distal bending section, depending on the procedure for which the specialized endoscope is designed.

Certain anatomical regions can be difficult to negotiate. For example, in the gastrointestinal (GI) tract, there are many bends, so that when the operator navigates to the target area, these bends cause the scope to rest in a specific orientation inside the lumen. During procedures like sphincterotomy or cancerous tissue resection, there may be certain approaches or scope orientations that may be more desirable so that the procedure is simpler, safer, and/or more effective.

For example, during sphincterotomy, a duodenoscope may be orientated by rotating the scope so that a papilla is located at approximately the 12 o'clock position prior to cannulation.

When a specialized endoscope has a telescoping camera, it may become challenging to maintain an orientation of vision as the outer flexible tube of the endoscope is steered and maneuvers are made. If the telescoping camera resides inside of an accessory channel, as the accessory channel is moved up, down, left, or right, the camera may not rotate in synchrony with the channel that the camera passes through. The lack of synchrony may leave the physician disoriented and make the medical procedure more difficult, because most procedures involve an instrument entering the field of view of the telescoping camera at a predictable angle.

SUMMARY

According to one aspect of the present disclosure, a medical device is provided. The medical device includes an elongate tube including a lumen extending therethrough, the elongate tube defining a longitudinal axis therethrough, the lumen including a surface with a first longitudinally-extending cross-sectional geometry. The medical device further includes a movable member extending longitudinally at least partially within the lumen, the movable member including a second lumen extending therethrough, the movable member including an outer surface with a second longitudinally-extending cross-sectional geometry. The medical device further includes a camera extending longitudinally at least partially within the second lumen. The first longitudinally-extending cross-sectional geometry and the second longitudinally-extending cross-sectional geometry are configured to prevent the movable member from rotating about the longitudinal axis relative to the elongate tube as the movable member is translated distally or proximally. The second longitudinally-extending cross-sectional geometry may be configured to complement the first longitudinally-extending cross-sectional geometry of the surface of the lumen. The second longitudinally-extending cross-sectional geometry may be non-axisymmetric. The first longitudinally-extending cross-sectional geometry may be non-axisymmetric. The second longitudinally-extending cross-sectional geometry may be elliptical, and the second longitudinally-extending cross-sectional geometry may include a major axis and a minor axis, the major axis larger than the minor axis. The first longitudinally-extending cross-sectional geometry may be elliptical; the first longitudinally-extending cross-sectional geometry may include a second major axis and a second minor axis, the second major axis larger than the minor axis; and the first longitudinally-extending cross-sectional geometry may be configured to complement the second longitudinally-extending cross-sectional geometry. The first longitudinally-extending cross-sectional geometry may be approximately circular; and the elongate tube may include attachments configured to complement the second longitudinally-extending cross-sectional geometry. The second longitudinally-extending cross-sectional geometry may include an oblong shape, a square shape, a detent, a groove, and/or a protruding feature. The first longitudinally-extending cross-sectional geometry may include an oblong shape, a square shape, a detent, a groove, a protruding feature, and/or an attachment configured to complement the second longitudinally-extending cross-sectional geometry. The movable member may include a shape set curve; the elongate tube may include a second shape curve configured to complement the shape set curve; and the shape set curve may be configured to bias the orientation of the movable member in the elongate tube. A second medical device may include a third lumen and the medical device housed in the third lumen, the third lumen defining a second longitudinal axis therethrough; and the medical device may be configured to prevent the medical device from rotating about the second longitudinal axis relative to the third lumen as the medical device is translated distally or proximally relative to the third lumen. The elongate tube may include a longitudinal slot connecting an outer elongate tube surface and the surface of the lumen; and the medical device may further include an outer clip, including an outer clip body at least partially encircling a circumference of the outer elongate tube surface; and a pin protruding inward radially from the outer clip body and configured to protrude through the longitudinal slot and to complement a detent or groove in the second longitudinally-extending cross-sectional geometry. The movable member may include a member longitudinal slot connecting the outer surface and the second lumen, and an anchor connected to the camera and protruding outward through the member longitudinal slot; and the anchor may be configured to prevent the camera from rotating about an axis parallel to the longitudinal axis relative to the elongate tube and/or from translating distally and proximally beyond a longitudinal dimension of the member longitudinal slot. The movable member may include one or more additional lumens extending therethrough configured to house a deflection cable, a suction device, an irrigation device, an insufflation device, a camera lens washing device, or a light-emitting diode, or to pass accessories. The surface of the lumen may include a plurality of indents equally spaced apart about a circumference of the lumen; and the outer surface of the movable member may include a plurality of protrusions, each of which is configured to confront an indent of the plurality of indents.

According to another aspect of the present disclosure, a medical device is provided. The medical device includes an elongate member including a lumen extending therethrough, the elongate tube defining a longitudinal axis therethrough, the lumen including a surface with a first longitudinally-extending cross-sectional geometry. The medical device further includes a movable member extending longitudinally at least partially within the lumen, the movable member including a second lumen extending therethrough, the movable member including an outer surface with a second longitudinally-extending cross-sectional geometry. The medical device further includes a camera extending longitudinally at least partially within the second lumen. The second longitudinally-extending cross-sectional geometry is configured to complement the first longitudinally-extending cross-sectional geometry of the surface of the lumen. The first longitudinally-extending cross-sectional geometry and the second longitudinally-extending cross-sectional geometry are configured to prevent the movable member from rotating about the longitudinal axis relative to the elongate tube as the movable member is translated distally or proximally. The second longitudinally-extending cross-sectional geometry may be non-axisymmetric. The second longitudinally-extending cross-sectional geometry may be elliptical; and the second longitudinally-extending cross-sectional geometry may include a major axis and a minor axis, the major axis larger than the minor axis. The second longitudinally-extending cross-sectional geometry may include an oblong shape, a square shape, a detent, a groove, and/or a protruding feature.

According to yet another aspect of the present disclosure, a medical device is provided. The medical device includes a lumen extending therethrough, the elongate tube defining a longitudinal axis therethrough, the lumen including a surface with a first longitudinally-extending cross-sectional geometry. The medical device further includes a movable member extending longitudinally at least partially within the lumen, the movable member including a second lumen extending therethrough, the movable member including an outer surface with a second longitudinally-extending cross-sectional geometry. The medical device further includes a camera extending longitudinally at least partially within the second lumen. The second longitudinally-extending cross-sectional geometry is elliptical and comprises a major axis and a minor axis, the major axis larger than the minor axis. The second longitudinally-extending cross-sectional geometry is configured to complement the first longitudinally-extending cross-sectional geometry of the surface of the lumen. The first longitudinally-extending cross-sectional geometry and the second longitudinally-extending cross-sectional geometry are configured to prevent the movable member from rotating about the longitudinal axis relative to the elongate tube as the movable member is translated distally or proximally.

Further areas of applicability will become apparent from the description provided herein. It should be understood that the description and specific examples are intended for purposes of illustration only and are not intended to limit the scope of the present disclosure.

DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts through the different views.

FIG. 6 illustrates a perspective view of a distal end portion of yet another example of a steerable endoscopic system according to the principles of the present disclosure, including an example of an outer clip;

FIG. 7 illustrates a perspective view of another example of an outer clip according to the principles of the present disclosure;

FIG. 8 illustrates a partial longitudinal cross-sectional view of a steerable endoscopic system according to the principles of the present disclosure, including a longitudinal cross-sectional view of an outer clip;

Figure 17:
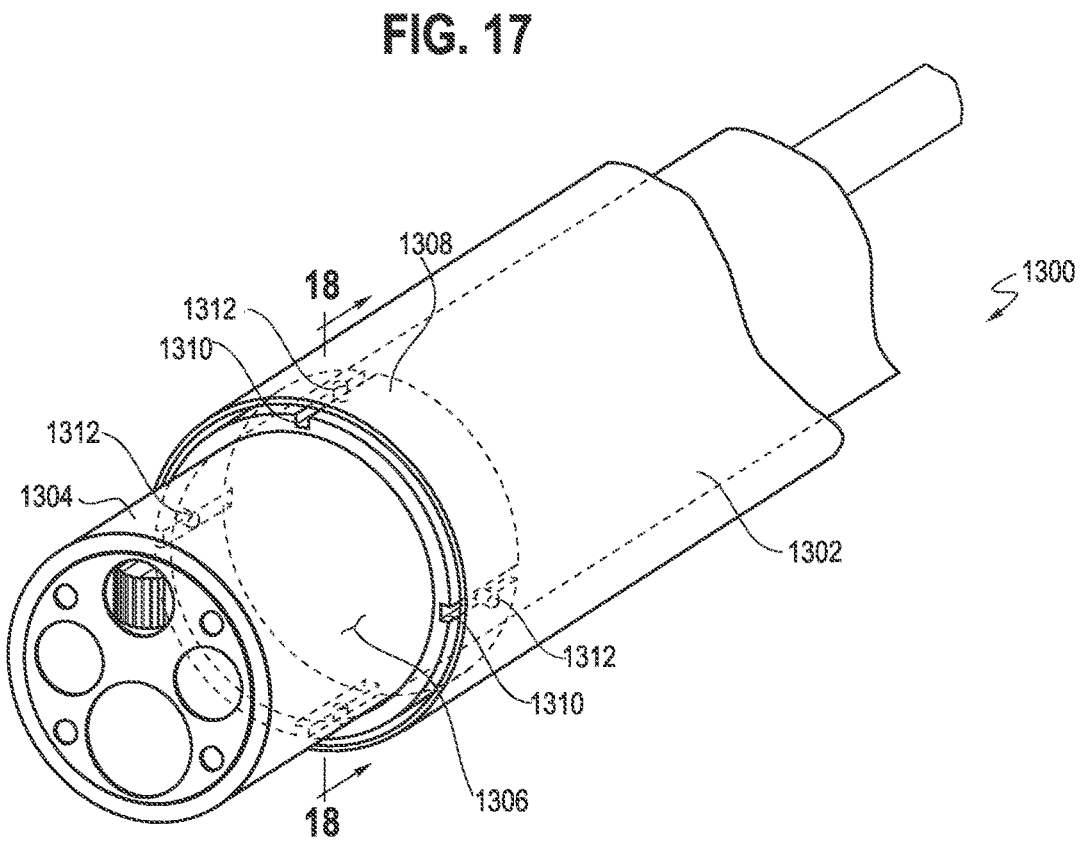
Figure 18:
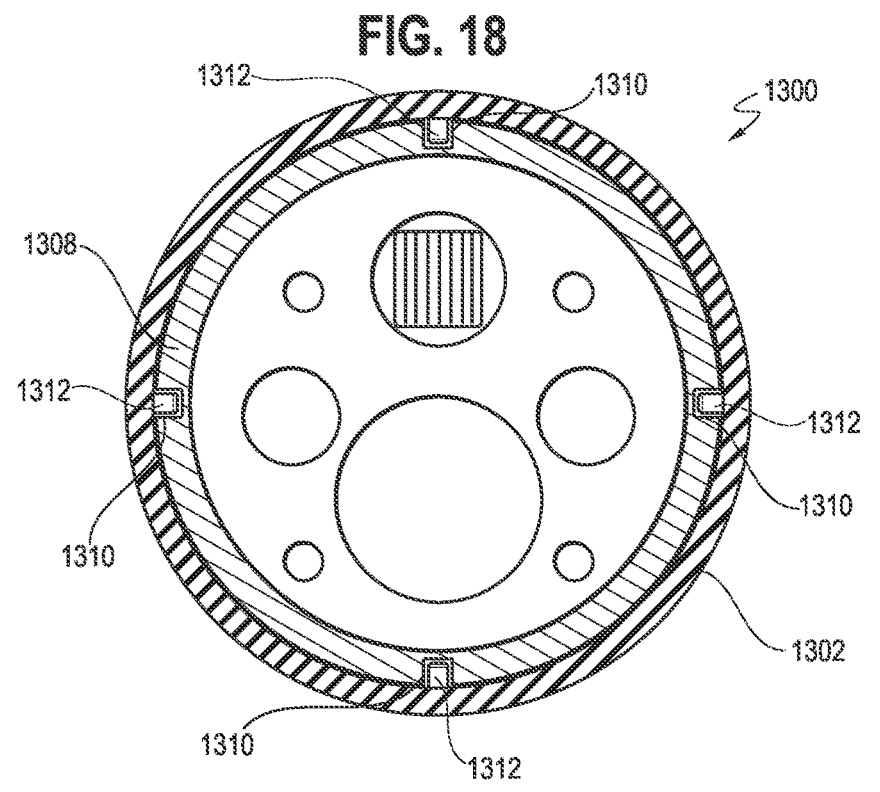
Figure 19:
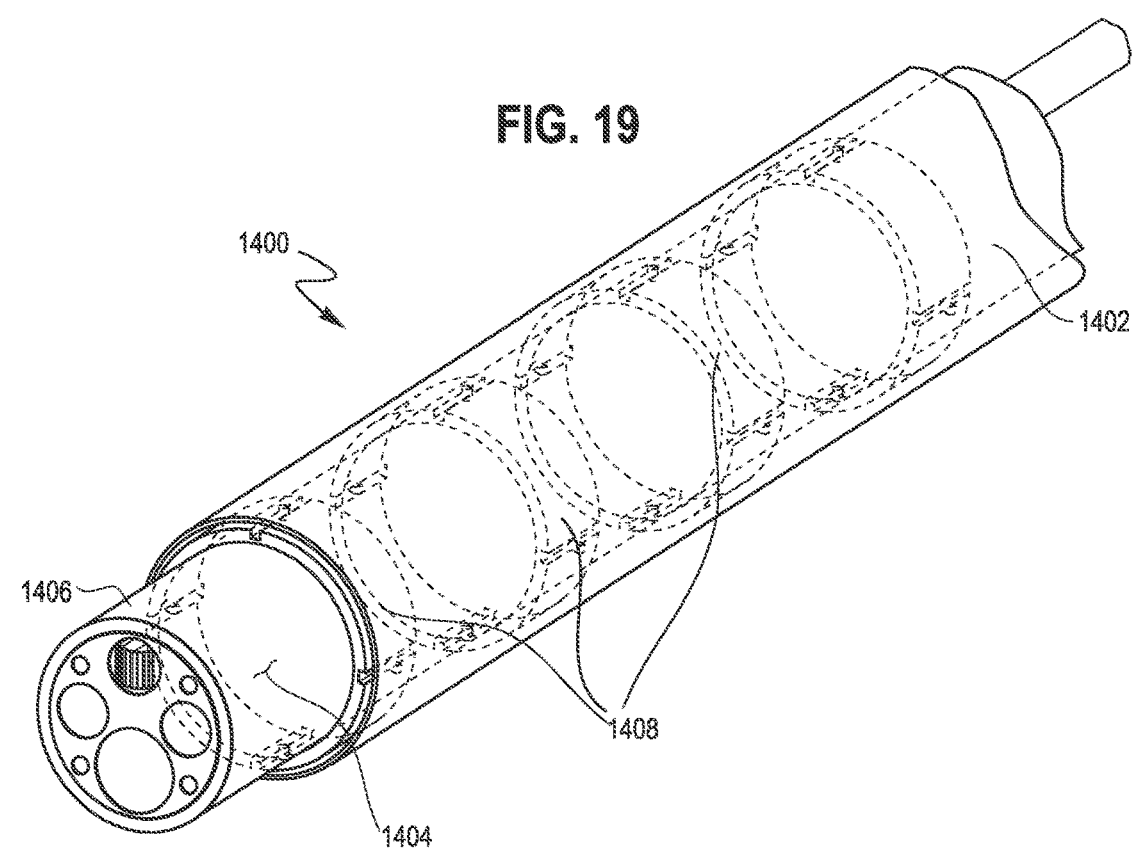
Figure 20:
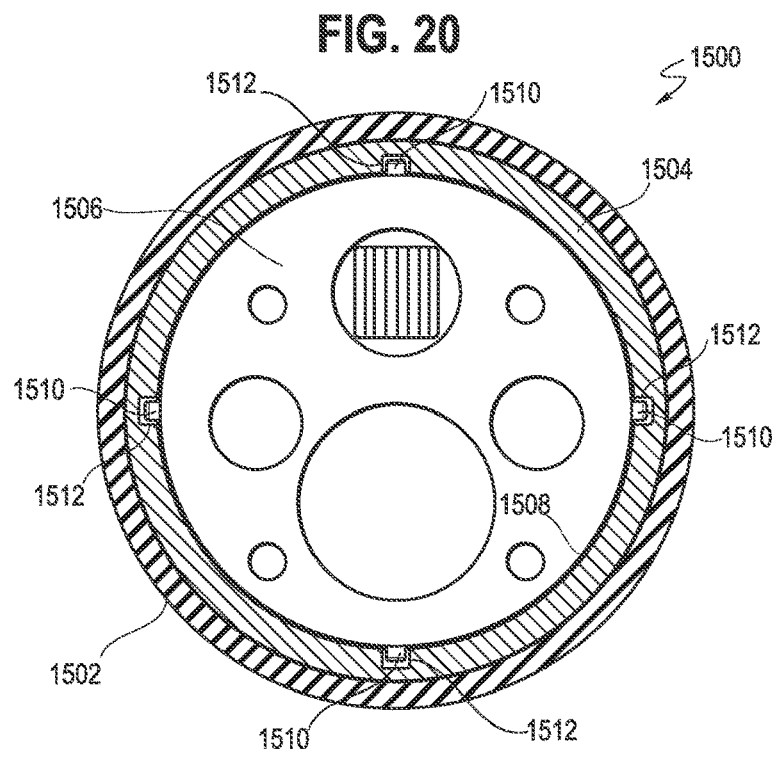
Figure 21:
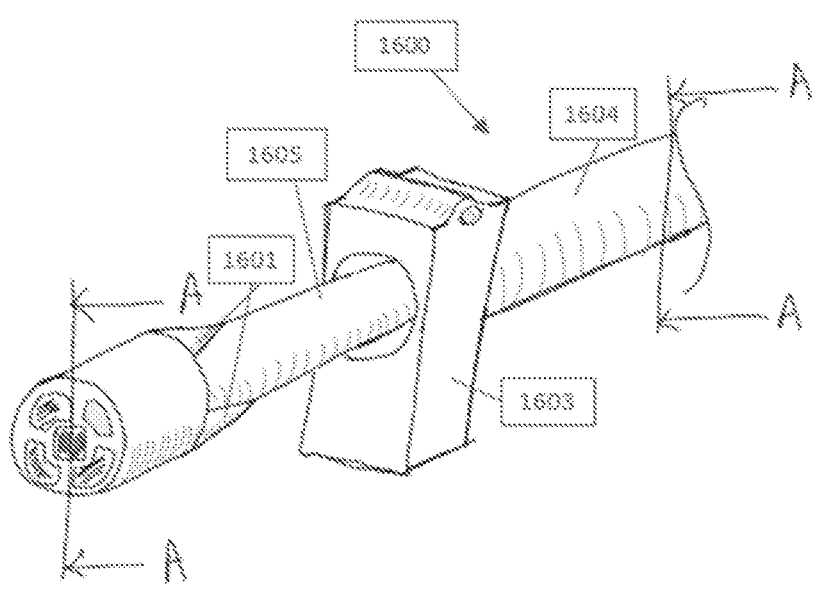
Figure 22:
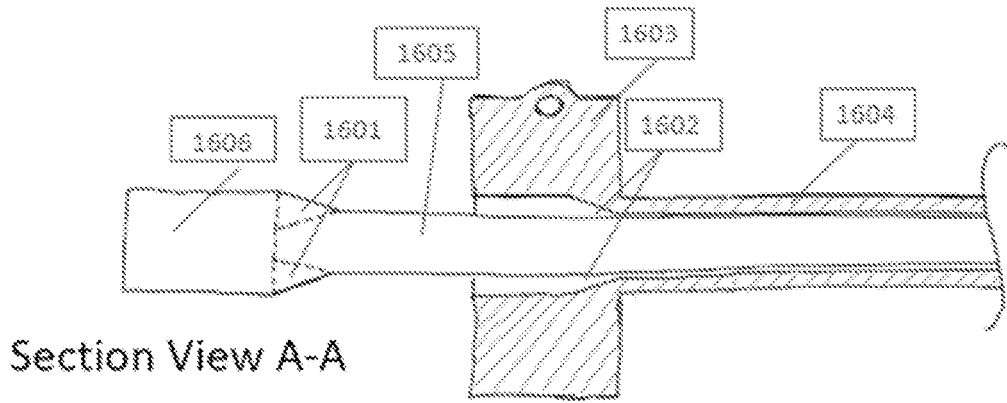
Figure 23:
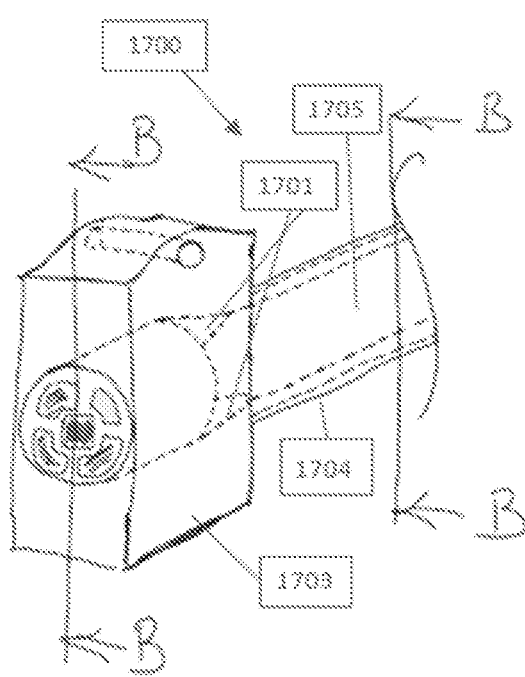
Figure 24:
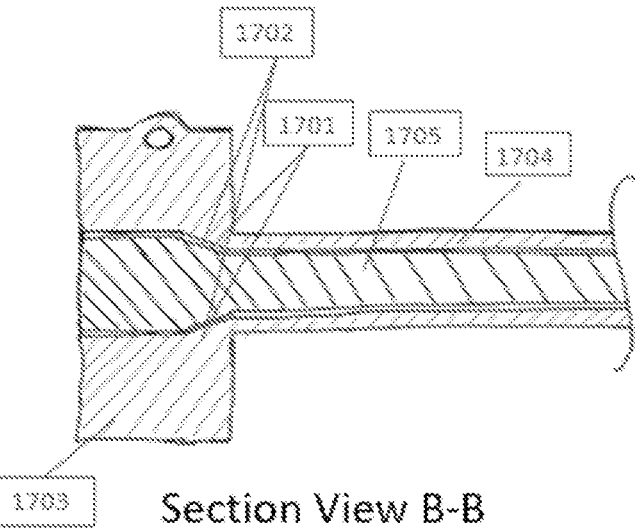
Figure 25:
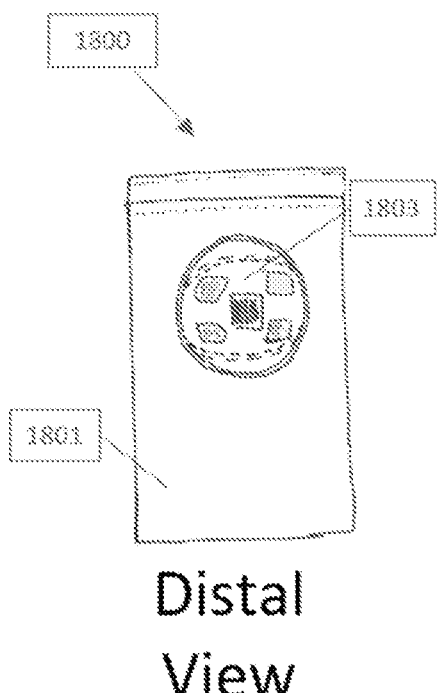
Figure 26:
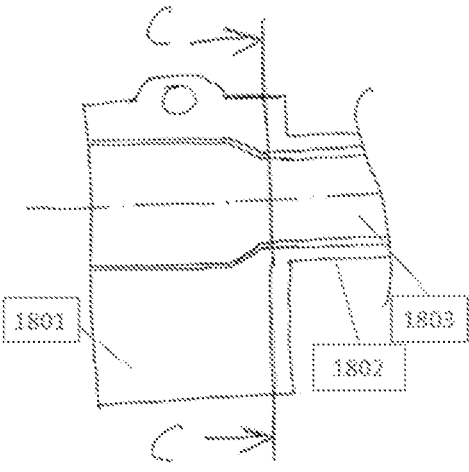
Figure 27:
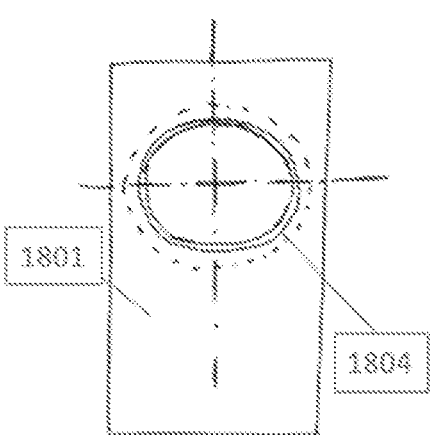
Figure 28:
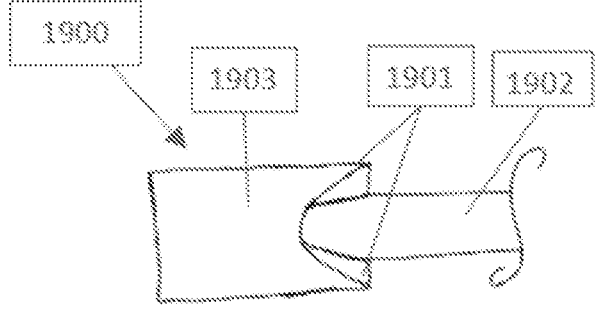
Figure 29:
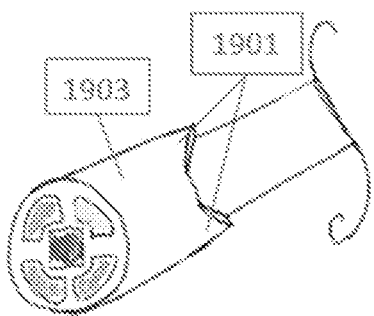
Figure 30:
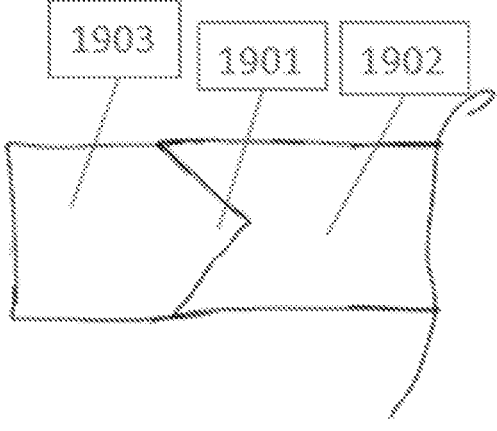

FIG. 17 illustrates a perspective view of the distal end portion of yet another example of a steerable endoscopic system including a plurality of pins protruding from the inner surface of the endoscope catheter, each pin of the plurality of pins fitting into a slot of a plurality of slots on a collar built into the outer surface of the endoscope catheter; according to the principles of the present disclosure;

FIG. 18 illustrates a distal end view of the example of a steerable endoscopic system of FIG. 17;

FIG. 19 illustrates a perspective view of yet another example of a steerable endoscope system including a plurality of collars built into the outer surface of the endoscope catheter and a plurality of sets of pins built into the inner surface of the endoscope catheter, according to the principles of the present disclosure;

FIG. 20 illustrates a distal end view of yet another example of a steerable endoscope system including a plurality of pins built into the outer surface of the endoscope catheter, and a plurality of slots in a collar built into the inner surface of the catheter sleeve, according to the principles of the present disclosure;

FIG. 21 illustrates a perspective view of a distal end of yet another example of a steerable endoscope system with an example of an endoscope catheter including male chevrons and an example of a catheter sleeve including female chevrons, according to the principles of the present disclosure;

FIG. 22 illustrates a longitudinal cross-sectional view of the example of the steerable endoscope system illustrated in FIG. 21 with the cross-section taken along axis A-A;

FIG. 23 illustrates a perspective view of a distal end of yet another example of a steerable endoscope system with an example of an endoscope catheter including male chevrons and an example of a catheter sleeve including female chevrons, according to the principles of the present disclosure;

FIG. 24 illustrates a longitudinal cross-sectional view of the example of the steerable endoscope system illustrated in FIG. 23 with the cross-section taken along axis B-B;

FIG. 25 illustrates a distal end view of yet another example of a steerable endoscope system with an endoscope catheter with an elliptical longitudinal cross-sectional geometry and a pivot arm with an elliptical longitudinal cross-sectional geometry, according to the principles of the present disclosure;

FIG. 26 illustrates a side view of a distal end of the example of the steerable endoscope system illustrated in FIG. 25;

FIG. 27 illustrates a longitudinal cross-sectional view of the example of the steerable endoscope system illustrated in FIGS. 26 and 27 with the cross-section taken along axis C-C;

FIG. 28 illustrates a side view of a distal end of yet another example of an endoscope catheter including male chevrons, according to the principles of the present disclosure;

FIG. 29 illustrates a perspective view of the example of the endoscope catheter illustrated in FIG. 28; and FIG. 30 illustrates a top view of the example of the endoscope catheter illustrated in FIGS. 28 and 29.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms "proximal" and "distal" will be used to describe the opposing axial ends of the device, as well as the axial ends of various component features. The term "proximal" is used in its conventional sense to refer to the end of the device (or component) that is closest to the medical professional during use of the assembly. The term "distal" is used in its conventional sense to refer to the end of the device (or component) that is initially inserted into the patient, or that is closest to the patient during use. The term "longitudinal" will be used to refer to an axis that aligns with the proximal-distal axis of the device (or component). The terms "radially" and "radial" will be used to refer to elements, surfaces, or assemblies relative to one another that may extend perpendicularly from a longitudinal axis. The terms "circumference," "circumferentially," and "circumferential" will be used to refer to elements, surfaces, or assemblies relative to one another encircling a longitudinal axis at a radius.

In the following discussion, the terms "non-axisymmetric" and "non-axisymmetrical" will be used herein to refer to an element having a shape that has a lack of axisymmetry, or a lack of rotational symmetry about a central axis.

As used herein, the terms "ellipse," "elliptical," and "elliptically-shaped" refer to a geometric shape in the form of a closed curve that results from the intersection of a cone or a cylinder by a plane. An ellipse has a major axis and a minor axis, each of about which the ellipse is axially symmetric. An ellipse surrounds two focal points, such that for all points on the ellipse, the sum of the distances to the two focal points is a constant. A circle is an example of an ellipse resulting from an intersection of a cone or a cylinder by a plane that is perpendicular to the height of the cone or the cylinder, and in which the two focal points are the same point.

The uses of the terms "a" and "an" and "the" and similar referents in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by the Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present description also contemplates other examples "comprising," "consisting of," and "consisting essentially of," the examples or elements presented herein, whether explicitly set forth or not.

In describing elements of the present disclosure, the terms $1^{st}$, $2^{nd}$ first, second, A, B, (a), (b), and the like may be used herein. These terms are only used to distinguish one element from another element, but do not limit the corresponding elements irrespective of the nature or order of the corresponding elements.

Unless otherwise defined, all term used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

As used herein, the term "about," when used in the context of a numerical value or range set forth means a variation of ±15%, or less, of the numerical value. For example, a value differing by ±15%, ±14%, ±10%, or ±5%, among others, would satisfy the definition of "about," unless more narrowly defined in particular instances.

Figure 1:
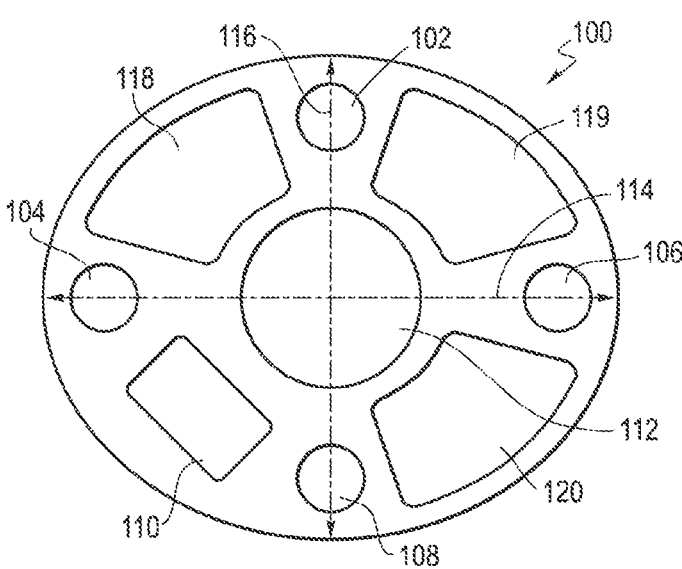
FIG. 1 illustrates a distal end view of an example of an endoscope catheter according to the principles of the present disclosure.

Referring to FIG. 1, a distal end view of an example of an endoscope catheter 100 is illustrated. Endoscope catheter 100 includes longitudinal deflection cable lumens 102, 104, 106, 108, camera lumen 112, and light-emitting diode lumen 110 parallel to the longitudinal axis. Endoscope catheter 100 further includes additional longitudinal lumens 118, 119, and 120, each of which is parallel to the longitudinal axis and may be independently configured for suction, irrigation, insufflation, camera lens washing, and/or passing accessories or configured to house a suction device, an irrigation device, an insufflation device, a camera lens washing device, or a light-emitting diode, or to pass accessories.

Endoscope catheter 100 has an outer surface that has a longitudinally-extending cross-sectional shape that is non-circular. Examples of non-circular longitudinally-extending cross-sectional shapes may include square, oblong, or elliptical. The longitudinally-extending cross-sectional shape of the outer surface of endoscope catheter 100 may include one or more longitudinal ridges, or a detent or a groove. Endoscope catheter 100 has an outer surface having a longitudinally-extending cross-sectional shape that is elliptical, wherein the longitudinally-extending cross-sectional shape of the outer surface of endoscope catheter 100 includes dimensions including major axis 114 and minor axis 116.

Figure 2:
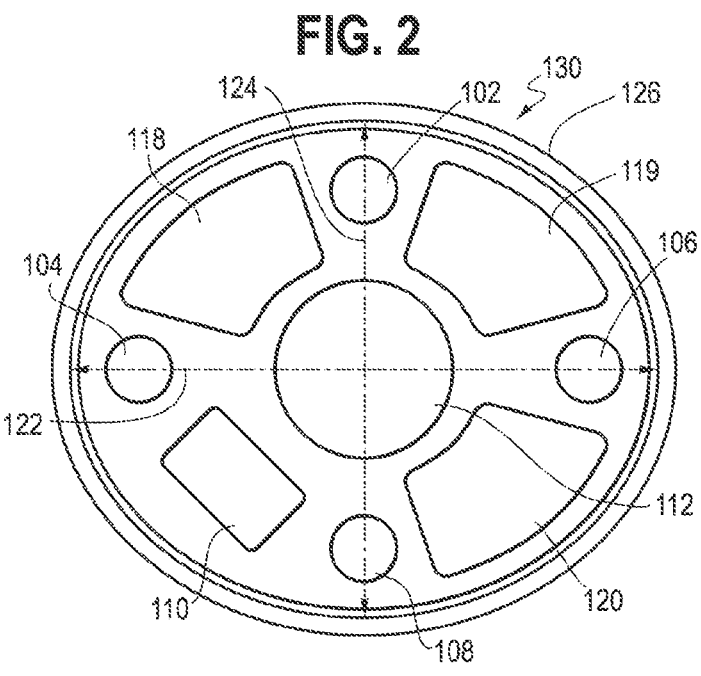
FIG. 2 illustrates a distal end view of an example of a steerable endoscopic system according to the principles of the present disclosure.

The longitudinally-extending cross-sectional shape of the outer surface of endoscope catheter 100 may provide a keying feature such that the longitudinally-extending cross-sectional shape of the outer surface of endoscope catheter 100 complements and/or approximates the longitudinally-extending cross-sectional shape of the inner surface of catheter sleeve 126 as illustrated in FIG. 2.

FIG. 2 illustrates steerable endoscopic system 130, including endoscope catheter 100 within catheter sleeve 126. Catheter sleeve 126 is an elongate tube that includes an inner surface including a keying feature such that the longitudinally-extending cross-sectional shape of the inner surface of catheter sleeve 126 complements and/or approximates the longitudinally-extending cross-sectional shape of the outer surface of endoscope catheter 100. Catheter sleeve 126 has an inner surface having a longitudinally-extending cross-sectional shape that is elliptical, wherein the longitudinally-extending cross-sectional shape of the inner surface of catheter sleeve 126 includes dimensions including major axis 122 and minor axis 124. Major axis 122 is larger than major axis 114 only such that endoscope catheter 100 may translate proximally and distally relative to catheter sleeve 126, but not such that endoscope catheter 100 rotates about the longitudinal axis relative to catheter sleeve 126. Minor axis 124 is larger than minor axis 116 only such that endoscope catheter 100 may translate proximally and distally relative to catheter sleeve 126, but not such that endoscope catheter 100 rotates about the longitudinal axis relative to catheter sleeve 126. The keying feature provided by the complementary longitudinally-extending cross-sectional shapes of the outer surface of endoscope catheter 100 and the inner surface of catheter sleeve 126 beneficially provides for an endoscope camera in camera lumen 112 to rotate in synchrony with catheter sleeve 126 and as endoscope catheter 100 translates distally and proximally or is advanced distally or retracted proximally relative to catheter sleeve 126. Further, endoscope catheter 100 is substantially precluded, substantially limited, or prevented from rotating relative to catheter sleeve 126 by the keying feature. By maintaining a rotational visual orientation of an endoscopic camera in camera lumen 112 relative to catheter sleeve 126 as steerable endoscopic system 130 is steered, steerable endoscopic system 130 may avoid disorientation and/or difficulty that is generally experienced by an operator of an endoscopic system without a keying feature.

In certain examples, a catheter sleeve of steerable endoscopic system 130 may have an inner surface with a longitudinally-extending cross-sectional shape that is circular while the longitudinally-extending cross-sectional shape of the outer surface of endoscope catheter 100 is elliptical. To provide a longitudinally-extending cross-sectional elliptical shape of the inner surface of a catheter sleeve so as to complement and/or approximate the elliptical longitudinally-extending cross-sectional shape of the outer surface of endoscope catheter 100, a secondary process may reshape the distal end of the catheter sleeve to complement and/or approximate the elliptical longitudinally-extending cross-sectional shape of the outer surface of endoscope catheter 100. The secondary process may include applying heat to the distal end of the catheter sleeve before reshaping the distal end of the catheter sleeve to complement and/or approximate the elliptical longitudinally-extending cross-sectional shape of the outer surface of endoscope catheter 100. The secondary process may further include using a tool to reshape the heated distal end of the catheter sleeve to complement and/or approximate the elliptical longitudi-nally-extending cross-sectional shape of the outer surface of endoscope catheter 100. Endoscope catheter 100 may extend distally from catheter sleeve 126 and retract proximally back into catheter sleeve 126. When endoscope catheter 100 is retracted fully into catheter sleeve 126, the distal end of endoscope catheter 100 is configured to result in a hard stop such that the distal end of endoscope catheter 100 is flush with the distal end of catheter sleeve 126. The distal end of endoscope catheter 100 cannot be retracted proximally past the distal end of catheter sleeve 126.

Figure 2A:
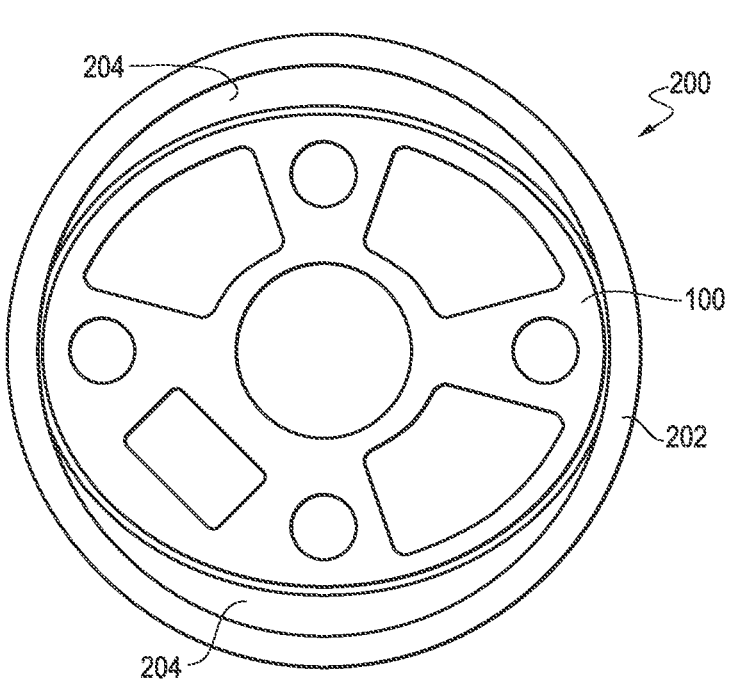
FIG. 2A illustrates a distal end view of another example of a steerable endoscopic system according to the principles of the present disclosure.

Referring to FIG. 2A, a distal end view of another example of a steerable endoscopic system 200 is illustrated. Steerable endoscopic system 200 includes endoscope cath-eter 100 having an outer surface with an elliptical longitu-dinally-extending cross-sectional shape, including dimen-sions including major axis 114 and minor axis 116. Steerable endoscopic system 200 further includes catheter sleeve 202 that is an elongate tube having an inner surface with a longitudinally-extending cross-sectional shape that is approximately circular. The inner cross-sectional diameter of catheter sleeve 202 may be larger than major axis 114, thereby precluding a camera in camera lumen 112 from rotating in synchrony with catheter sleeve 202. Steerable endoscopic system 200 includes a keying feature in the form of attachments 204, which may be configured to supplement the inner surface of catheter sleeve 202 such that the inner surface of catheter sleeve 202, with attachments 204, complements and/or approximates the elliptical longitudi-nally-extending cross-sectional outer surface of endoscope catheter 100. As illustrated in FIG. 2A, attachments 204 may supplement the dimensions of the circular inner surface of catheter sleeve 202 such that the diameter of the circular inner surface of catheter sleeve 202 is decreased to slightly larger than the dimension of minor axis 116, thereby pre-cluding endoscope catheter 100 from rotating relative to catheter sleeve 202. In other examples, attachments 204 may supplement the inner surface of catheter sleeve 202 by including profiles configured to complement or approximate one or more longitudinal ridges, grooves, detents, or oblong or square shapes in the outer surface of endoscopic catheter 100.

Figure 3:
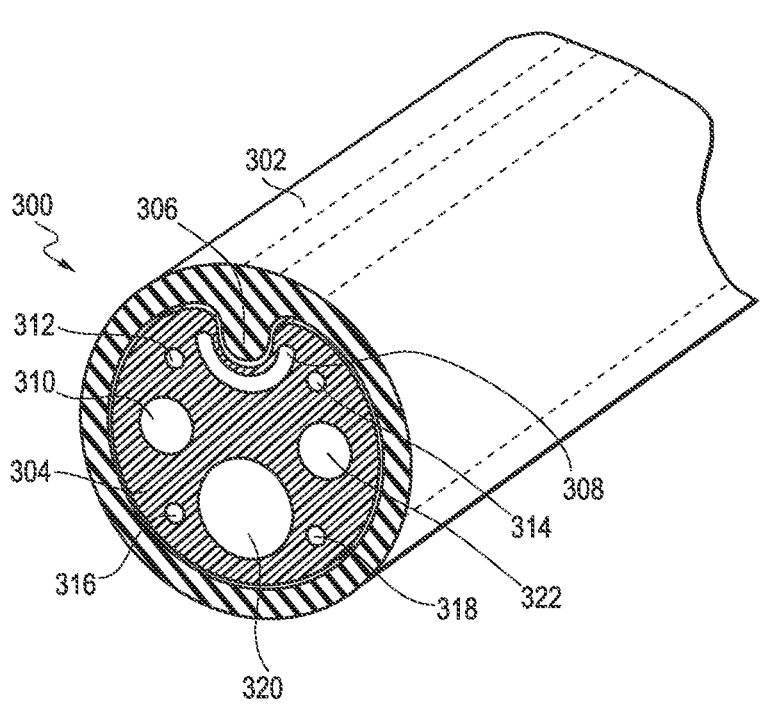
FIG. 3 illustrates a perspective view of a distal end portion of yet another example of a steerable endoscopic system according to the principles of the present disclosure.

Referring to FIG. 3, a perspective view of a distal end portion of yet another example of a steerable endoscopic system 300 is illustrated. Steerable endoscopic system 300 includes endoscope catheter 304 that includes a keying feature such that the outer surface of endoscope catheter 304 has a longitudinally-extending cross-sectional non-axisym-metric shape. The keying feature may include a groove or recess in the outer surface of endoscope catheter 304 parallel to the longitudinal axis of steerable endoscopic system 300. Endoscope catheter 304 includes longitudinal deflection cable lumens 312, 314, 316, 318, camera lumen 308, and light-emitting diode lumen 310, each of which is parallel to the longitudinal axis. Endoscope catheter 304 further includes additional longitudinal lumens 320 and 322, each of which is parallel to the longitudinal axis and may be independently configured for suction, irrigation, insufflation, camera lens washing, and/or passing accessories or config-ured to house a suction device, an irrigation device, an insufflation device, a camera lens washing device, or a light-emitting diode, or to pass accessories. Steerable endo-scopic system 300 includes catheter sleeve 302 that is an elongate tube that includes an inner surface having a longi-tudinally-extending cross-sectional non-axisymmetric shape including a pin 306 integral to catheter sleeve 302. Pin 306 protrudes inward from the inner surface of catheter sleeve 302 parallel to the longitudinal axis and complements and/or approximates the groove or recess in the outer surface of endoscope catheter 304 such that rotational visual orienta-tion of endoscope catheter 304 is maintained as steerable endoscopic system 300 is steered and endoscope catheter 304 translates proximally and distally or is advanced distally or retracted proximally relative to catheter sleeve 302.

Figure 4:
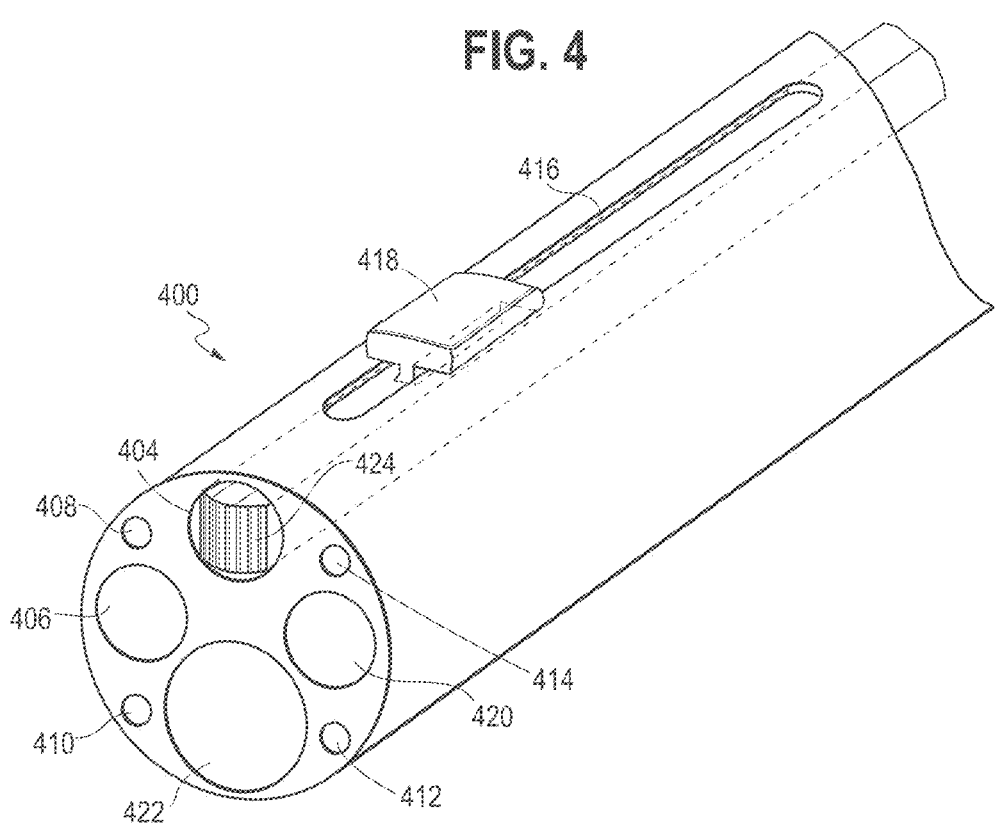
FIG. 4 illustrates a perspective view of a distal end portion of another example of an endoscope catheter according to the principles of the present disclosure.

Referring to FIG. 4, a perspective view of a distal end portion of yet another example of an endoscope catheter 400 is illustrated. Endoscope catheter 400 includes longitudinal deflection cable lumens 408, 410, 412, 414, camera lumen 404, and light-emitting diode lumen 406, each of which is parallel to the longitudinal axis. Endoscope catheter 400 further includes additional longitudinal lumens 420 and 422, each of which is parallel to the longitudinal axis and may be independently configured for suction, irrigation, insufflation, camera lens washing, and/or passing accessories or config-ured to house a suction device, an irrigation device, an insufflation device, a camera lens washing device, or a light-emitting diode, or to pass accessories. Telescoping camera 424 may be housed in camera lumen 404 and may be advanced distally or retracted proximally through camera lumen 404 relative to endoscope catheter 400. Endoscope catheter 400 includes a keying feature that may include an anchor 418 and a slot 416. Slot 416 is an opening connecting the outer surface of endoscope catheter 400 and camera lumen 404 that extends longitudinally and proximally, par-allel to the longitudinal axis of endoscope catheter 400, from a point proximal to the distal surface of endoscope catheter 400. Anchor 418 protrudes from telescoping camera 424 through slot 416 such that the rotational visual orientation of telescoping camera 424 is maintained. Telescoping camera 424 may advance distally and retract proximally relative to endoscope catheter 400 along the longitudinal dimension of slot 416. Anchor 418 acts as a rotational stop to prevent telescoping camera 424 from rotating in camera lumen 404 relative to endoscope catheter 400 and as a translational stop to prevent telescoping camera 424 from advancing distally or retracting proximally beyond the range of longitudinal distance permitted by the longitudinal dimension of slot 416.

Figure 5:
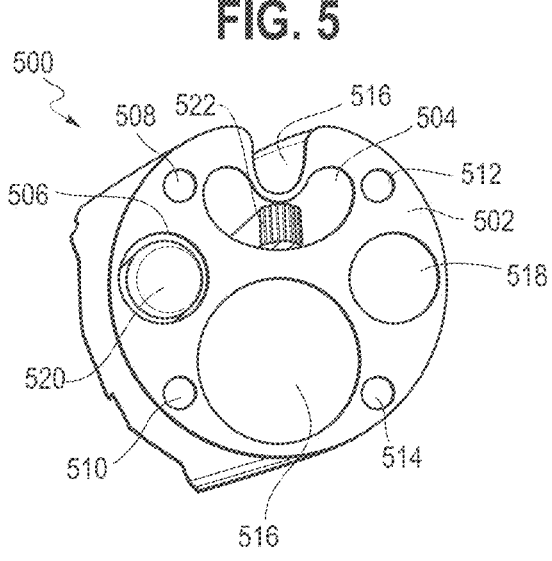
FIG. 5 illustrates a perspective view of a distal end portion of yet another example of an endoscope catheter according to the principles of the present disclosure, including a camera and a light-emitting diode.

Referring to FIG. 5, a perspective view of a distal end portion 502 of yet another example of an endoscope catheter 500 is illustrated. Endoscope catheter 500 includes a keying feature such that the outer surface of endoscope catheter 500 has a longitudinally-extending cross-sectional non-axisym-metric shape. The keying feature may include a groove 516 in the outer surface of endoscope catheter 500 parallel to the longitudinal axis of endoscope catheter 500. Groove 516 complements and/or approximates an inner surface of a catheter sleeve that has a longitudinally-extending cross-sectional non-axisymmetric shape that includes a pin inte-gral to the catheter sleeve and protruding inward from the inner surface of the catheter sleeve parallel to the longitu-dinal axis of the endoscope catheter. Endoscope catheter 500 includes longitudinal deflection cable lumens 508, 510, 512, 514, camera lumen 504, and light-emitting diode lumen 506, each of which is parallel to the longitudinal axis. Camera lumen 504 includes telescoping camera 522. Light-emitting diode lumen 506 includes light-emitting diode 520. Endo-scope catheter 500 further includes additional longitudinal lumens 516 and 518, each of which is parallel to the longitudinal axis and may be independently configured for suction, irrigation, insufflation, camera lens washing, and/or passing accessories or configured to house a suction device, an irrigation device, an insufflation device, a camera lens washing device, or a light-emitting diode, or to pass accessories.

Referring to FIG. 6, a perspective view of a distal end portion of yet another example of a steerable endoscopic system 600 including an example of an outer clip 606 is illustrated. Steerable endoscope system 600 includes telescoping endoscope catheter 604 and outer clip 606, which is attached to telescoping endoscope catheter 604 by connector 610 and button 608. Button 608 is configured to engage with telescoping endoscope catheter 604. Connector 610 may pass radially through slot 612 in catheter sleeve 602. Outer clip 606 may substantially encircle the circumference of catheter sleeve 602. Outer clip 606 may be part of and/or attached to a larger scope device, in which telescoping endoscope catheter 604 and catheter sleeve 602 may be configured as an accessory housed within a lumen. Outer clip 606 may prevent, substantially preclude, or substantially limit telescoping endoscope catheter 604 and catheter sleeve 602 from rotating about the longitudinal axis of such an accessory lumen housing steerable endoscope system 600 relative to the larger scope device. Telescoping endoscope catheter 604 includes longitudinal deflection cable lumens 618, 620, 622, 624, camera lumen 630, and light-emitting diode lumen 616, each of which is parallel to the longitudinal axis. Camera lumen 630 includes camera 614. Telescoping endoscope catheter 604 further includes additional longitudinal lumens 626 and 628, each of which is parallel to the longitudinal axis and may be independently configured for suction, irrigation, insufflation, camera lens washing, and/or passing accessories or configured to house a suction device, an irrigation device, an insufflation device, a camera lens washing device, or a light-emitting diode, or to pass accessories. Telescoping endoscope catheter 604 may be advanced distally or retracted proximally through catheter sleeve 602. Steerable endoscopic system 600 is housed within an accessory lumen of a larger device, and endoscope catheter 604 and catheter sleeve 602 may be advanced distally and retracted proximally together. Slot 612 is an opening in catheter sleeve 602 that extends longitudinally and proximally, parallel to the longitudinal axis of steerable endoscopic system 600, from a point proximal to the distal surface of telescoping endoscope catheter 604. Camera 614 may not advance distally and retract proximally relative to telescoping endoscope catheter 604 along the longitudinal dimension of slot 612, but instead may advance distally and retract proximally with telescoping endoscope catheter 604 along the longitudinal dimension of slot 612. Outer clip 606 may act as a rotational stop to prevent telescoping endoscope catheter 604 from rotating relative to catheter sleeve 602 and as a translational stop to prevent telescoping endoscope catheter 604 from advancing distally or retracting proximally relative to catheter sleeve 602 beyond the range of longitudinal distance permitted by the longitudinal dimension of slot 612. Outer surface of telescoping endoscope catheter 604 may have a longitudinally-extending cross-sectional shape that complements and/or approximates the longitudinally-extending cross-sectional shape of inner surface of catheter sleeve 602. In the example of steerable endoscopic system 600 illustrated in FIG. 6, the outer surface of telescoping endoscope catheter 604 has a circular longitudinally-extending cross-sectional shape that complements and/or approximates the circular longitudinally-extending cross-sectional shape of the inner surface of catheter sleeve 602.

Referring to FIG. 7, a perspective view of another example of an outer clip 700 is illustrated. Outer clip 700 includes an arcuate outer clip body 702 that has a substantially circular longitudinally-extending cross-sectional shape that is configured to substantially encircle an outer circumference of a catheter sleeve of a steerable endoscopic system. Outer clip 700 may be part of and/or attached to a larger scope device, in which a telescoping endoscope catheter and a catheter sleeve may be configured as an accessory housed within a lumen. The longitudinally-extending cross-sectional shape of outer clip 700 is symmetrical, and at the cross-sectional arcuate mid-point of outer clip body 702 is pin 704 protruding radially inward from outer clip body 702 parallel to the longitudinal axis of the steerable endoscopic system that includes outer clip 700. Pin 704 extends along the entire longitudinal dimension of outer clip 700. Pin 704 may complement and/or approximate a keying feature of a telescoping endoscope catheter and/or a catheter sleeve such that a camera in a camera lumen of an endoscope catheter maintains rotational visual orientation as the steerable endoscopic system including outer clip 700 is steered and a telescoping endoscope catheter of the steerable endoscopic system including outer clip 700 is advanced distally and retracted proximally in the catheter sleeve of the steerable endoscopic system including outer clip 700.

Referring to FIG. 8, a partial longitudinal cross-sectional view of a steerable endoscopic system 800 including a partial longitudinal cross-sectional view of outer clip 700 is illustrated. Outer clip 700 includes an arcuate outer clip body 702 that has a substantially circular cross-sectional shape that is configured to substantially encircle an outer circumference of catheter sleeve 802. The longitudinally-extending cross-sectional shape of outer clip 700 is symmetrical, and at the cross-sectional arcuate mid-point of outer clip body 702 is pin 704 protruding radially inward from outer clip body 702 parallel to the longitudinal axis of steerable endoscopic system 800. Pin 704 extends along the entire longitudinal dimension of outer clip 700. Endoscope catheter 804 includes a keying feature that may be a longitudinal slot 806 in outer surface of endoscope catheter 804 such that the outer surface of endoscope catheter 804 has a longitudinally-extending cross-sectional shape that is non-axisymmetric. Pin 704 protrudes through a longitudinal slot in catheter sleeve 802 and complements and/or approximates slot 806 of endoscope catheter 804 by occupying slot 806. Slot 806 may connect the outer surface of endoscope catheter 804 and a longitudinal lumen extending longitudinally through endoscope catheter 804 parallel to the longitudinal axis and deflection cable lumens 808, 810.

Figures 9, 10, 11, 12:
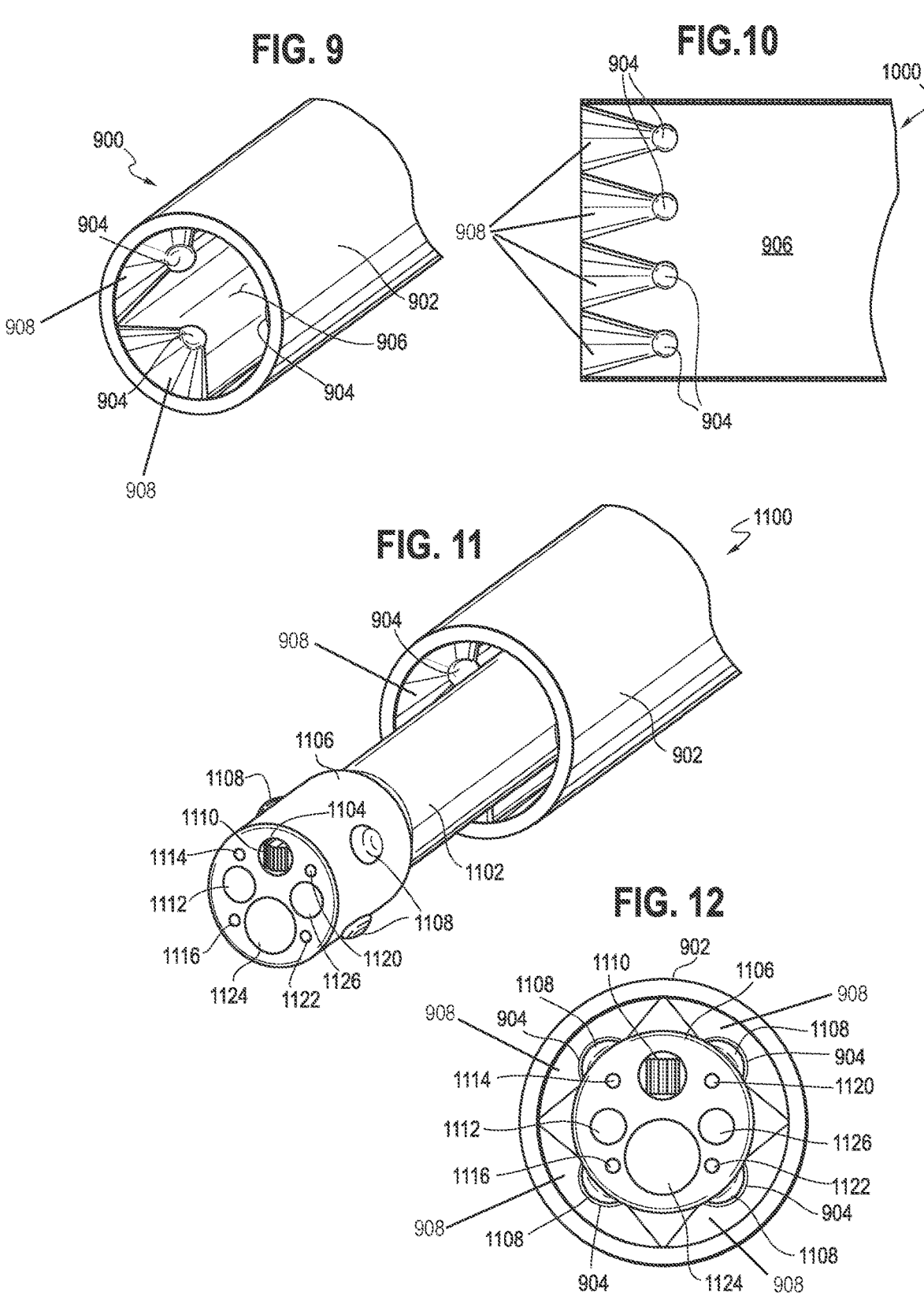
FIG. 9 illustrates a perspective view of a distal end portion of an example of a catheter sleeve according to the principles of the present disclosure.
FIG. 10 illustrates a view of an inner surface of the distal end portion of the example of catheter sleeve of FIG. 9 if the catheter sleeve were cut open longitudinally and laid flat.
FIG. 11 illustrates a perspective view of a distal end portion of yet another example of a steerable endoscopic system according to the principles of the present disclosure, including the catheter sleeve of FIG. 9.
FIG. 12 illustrates a distal end view of the example of the steerable endoscopic system illustrated in FIG. 11.

Referring to FIG. 9, a perspective view of a distal end portion of another example of a catheter sleeve 900 is illustrated. Catheter sleeve 900 is an elongate tube that includes outer surface 902 with a longitudinally-extending cross-sectional shape that is circular. Inner surface 906 of catheter sleeve 900 includes a plurality of indents 904 that are evenly spaced apart around the distal end of inner surface 906. Examples of plurality of indents 904 may include two, three, four, five, six, seven, eight, nine, or ten, or more indents evenly spaced apart around the distal end of inner surface 906. Inner surface 906 of catheter sleeve 900 includes a plurality of ramps 908, each ramp of which extends from the distal end of catheter sleeve 900 to an indent of plurality of indents 904. Plurality of ramps 908 are configured to lead into plurality of indents 904. The example of catheter sleeve 900 shown in FIG. 9 includes a plurality of indents 904 including four indents evenly spaced apart about the distal end of inner surface 906 at 90° increments.

A view of inner surface 906 of the distal end portion of catheter sleeve 900 if catheter sleeve 900 were cut open longitudinally and laid flat as an opened catheter sleeve 1000 is illustrated in FIG. 10. Opened catheter sleeve 1000 includes a plurality of indents 904 equally spaced apart about the distal end of inner surface 906.

Referring to FIG. 11, a perspective view of a distal end portion of yet another example of a steerable endoscopic system 1100 including catheter sleeve 900 of FIG. 9 is illustrated. Steerable endoscopic system 1100 includes endoscope catheter 1102. Endoscopic catheter includes distal outer surface 1106. Distal portion of endoscope catheter 1102 may have a different longitudinal cross-sectional diameter than proximal portions of endoscope catheter 1102. As shown in FIG. 11, the example of endoscope catheter 1102 has a distal portion having a larger cross-sectional diameter than the remainder of endoscope catheter 1102. Endoscope catheter 1102 includes longitudinal deflection cable lumens 1114, 1116, 1120, 1122, camera lumen 1104, and light-emitting diode lumen 1112, each of which is parallel to the longitudinal axis. Camera lumen 1104 includes camera 1110. Endoscope catheter 1102 further includes additional longitudinal lumens 1124 and 1126, each of which is parallel to the longitudinal axis and may be independently configured for suction, irrigation, insufflation, camera lens washing, and/or passing accessories or configured to house a suction device, an irrigation device, an insufflation device, a camera lens washing device, or a light-emitting diode, or to pass accessories. Endoscope catheter 1102 includes a keying feature on distal outer surface 1106 including a plurality of protrusions 1108 that are equally spaced apart about a circumference of distal outer surface 1106. Examples of plurality of protrusions 1108 may include two, three, four, five, six, seven, eight, nine, or ten, or more protrusions evenly spaced apart about a circumference of distal outer surface 1106. The example of endoscope catheter 1102 shown in FIG. 11 includes a plurality of protrusions 1108 including four protrusions evenly spaced apart about distal outer surface 1106 at 90° increments. Plurality of ramps 908 are configured to cause outer surface 902 to radially expand about plurality of protrusions 1108 and give a user a tactile snap into place of plurality of protrusions 1108 into plurality of indents 904 when distal outer surface 1106 is seated in its "locked" or "home" position illustrated by FIG. 15. The number of protrusions constituting an example of plurality of protrusions 1108 of endoscope catheter 1102 in an example of steerable endoscopic system 1100 equals the number of indents constituting plurality of indents 904 of catheter sleeve 900 in the example of steerable endoscopic system 1100. Each protrusion of plurality of protrusions 1108 of endoscope catheter 1102 is configured to confront an indent of plurality of indents 904 when endoscope catheter 1102 is retracted proximally into catheter sleeve 900 such that rotational visual orientation of endoscope catheter 1102 is maintained as steerable endoscopic system 1100 is steered. FIG. 12 illustrates a distal end view of steerable endoscope system 1100.

Figure 13:
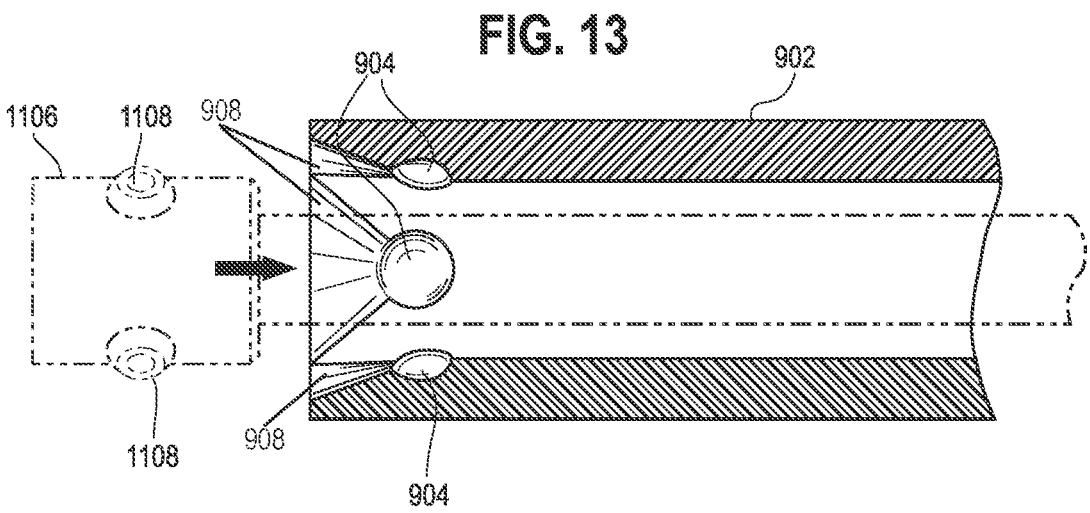
FIG. 13 illustrates a side view of the distal end portion of the example of the steerable endoscopic system illustrated in FIG. 11.
Figure 14:
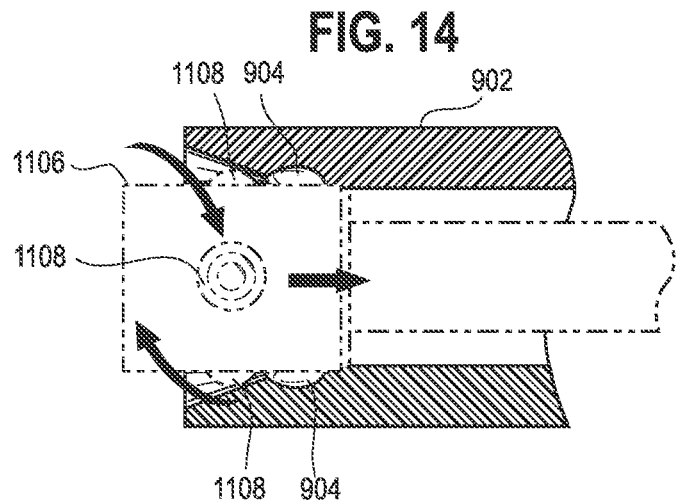
FIG. 14 illustrates a side view of the distal end portion of the example of the steerable endoscopic system illustrated in FIG. 13 with the catheter inserted proximally into the catheter sleeve and rotated circumferentially relative to the position of the catheter in FIG. 13.
Figure 15:
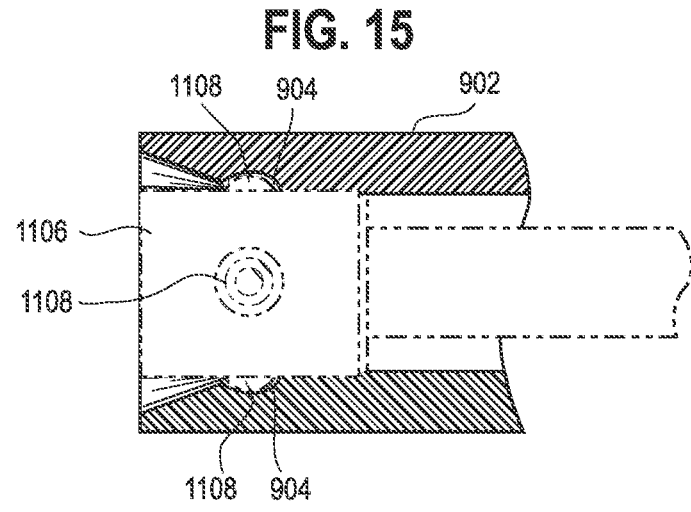
FIG. 15 illustrates a side view of the distal end portion of the example of the steerable endoscopic system illustrated in FIG. 13 with the catheter inserted proximally into the catheter sleeve relative to the position of the catheter in FIG. 14 such that the distal ends of the catheter and the catheter sleeve are flush.

Referring to FIGS. 13-15, side views of the distal end portion of steerable endoscopic system 1100 are illustrated. As shown in FIG. 13, plurality of protrusions 1108 of endoscope catheter 1102 are positioned circumferentially between plurality of indents 904 of catheter sleeve 900. As distal end portion of endoscopic catheter 1102 is retracted proximally into catheter sleeve 900, endoscope catheter 1102 is rotated circumferentially in a direction and catheter sleeve 900 is rotated circumferentially in a second direction opposite the direction, as illustrated in FIG. 14. Each protrusion of plurality of protrusions 1108 confronts an indent of plurality of indents 904 such that distal end surface of endoscope catheter 1102 is flush with distal end surface of catheter sleeve 900, and endoscope catheter 1102 cannot rotate further relative to catheter sleeve 900. The plurality of protrusions 1108 thereby act as a keying feature such that rotational visual orientation of endoscope catheter 1102 is maintained as steerable endoscopic system 1100 is steered.

Figure 16:
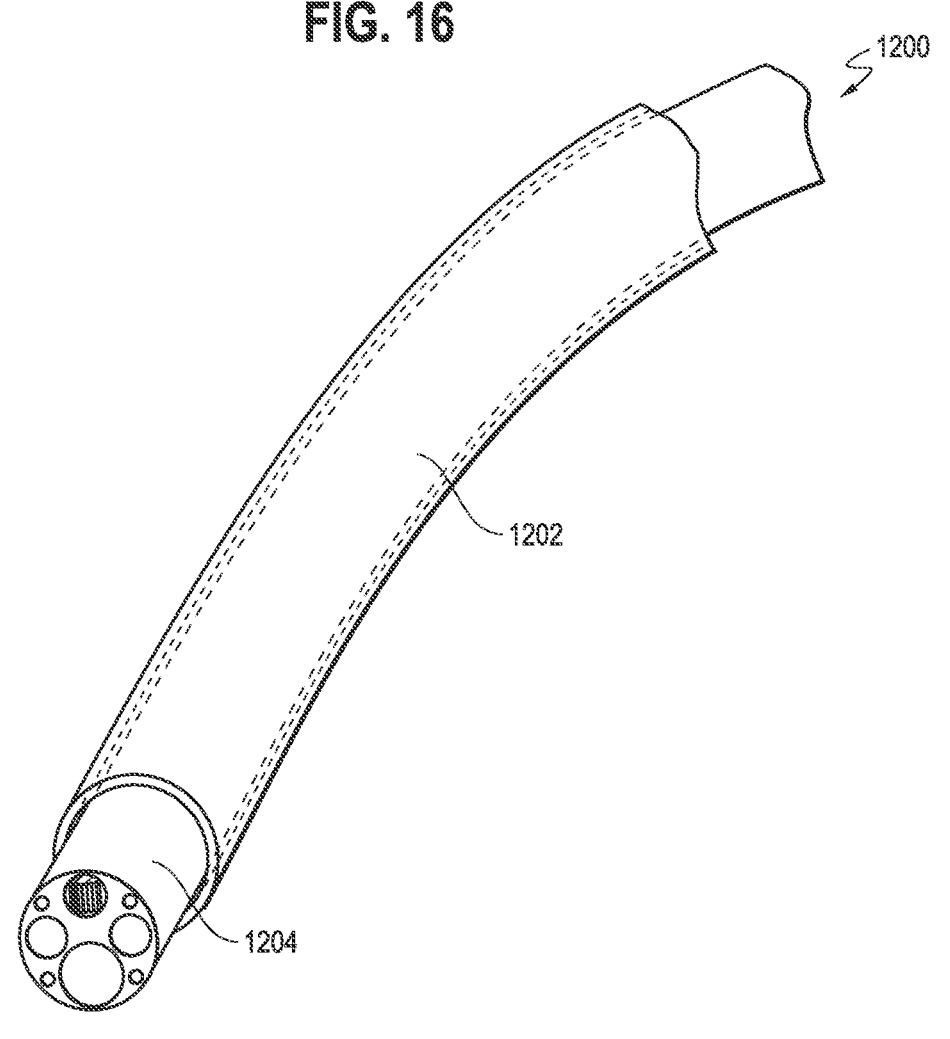
FIG. 16 illustrates a perspective view of the distal end portion of yet another example of a steerable endoscopic system including a shape set curve according to the principles of the present disclosure.

Referring to FIG. 16, a perspective view of the distal end portion of steerable endoscope system 1200 includes endoscope catheter 1204 with a curved shape set feature. Endoscope catheter 1204 is within catheter sleeve 1202 which has a curved shape set feature similar to endoscope catheter 1204 and which may complement and/or approximate the curved shape set feature of endoscope catheter 1204. The curved shape set feature of the endoscope catheter 1204 serves as a keying feature by biasing the orientation of endoscope catheter 1204 within the similarly curved shape set feature of catheter sleeve 1202 such that rotational visual orientation of endoscope catheter 1204 is maintained as steerable endoscopic system 1200 is steered.

In examples of steerable endoscopic systems of the present disclosure, a keying feature may be configured to substantially preclude or substantially limit or prevent rotation of an endoscope catheter relative to a catheter sleeve, but the keying feature may not extend longitudinally. For example, an inner surface of a catheter sleeve may include evenly spaced protruding features or pins at a certain circumference of the catheter sleeve that are configured to pass through complementing, equally evenly spaced slots in a collar integral to and extending outward radially from the outer surface of the endoscope catheter at a certain circumference. The collar may be configured to confront the protruding features or pins and consequently arrest translational movement of the endoscope catheter proximally or distally relative to the catheter sleeve, except when the protruding features or pins are aligned with the slots in the collar. When the protruding features or pins are aligned with the slots in the collar, the endoscope catheter may translate distally or proximally relative to the catheter sleeve as the protruding features or pins pass through the slots in the collar. A catheter sleeve may have a plurality of circumferences at which the protruding features are located along the longitudinal dimension of the catheter sleeve, and an endoscope catheter may have a plurality of collars along the longitudinal dimension of the endoscope catheter. In other examples, the inner surface of a catheter sleeve may have a narrower diameter at a certain circumference due to a collar integral to and protruding from the inner surface of the catheter sleeve, except for evenly spaced slots configured to complement equally evenly spaced protruding features or pins extending from and integral to opposite sides of an outer surface of an endoscope catheter. The narrower diameter of the longitudinal cross-section including the collar may be configured to confront the protruding features or pins and consequently arrest translational movement of the endoscope catheter proximally or distally relative to the catheter sleeve, except when the protruding features or pins are aligned with the slots in the collar. When the protruding features or pins are aligned with the slots in the collar, the endoscope catheter may translate distally or proximally relative to the catheter sleeve as the protruding features or pins pass through the slots in the collar. A catheter sleeve may have a plurality of circumferences at which the collars are located along the longitudinal dimension of the catheter sleeve, and an endoscope catheter may have a plurality of circumferences at which evenly spaced protruding features or pins are protruding.

Referring to FIG. 17, a perspective view of a distal end portion of yet another example of a steerable endoscopic system 1300 is illustrated. Steerable endoscopic system 1300 includes endoscope catheter 1304 that includes a keying feature such that outer surface 1306 of endoscope catheter 1304 includes collar 1308 integral to endoscope catheter 1304 and protruding from outer surface 1306 around a circumference of outer surface 1306. Collar 1308 includes a plurality of slots 1310 cut out of collar 1308 evenly spaced about the circumference. The example of steerable endoscopic system 1300 shown in FIG. 17 includes plurality of slots 1310 evenly spaced at 90 degrees about the circumference of collar 1308, as illustrated in the distal end view of steerable endoscopic system 1300 shown in FIG. 18. Steerable endoscopic system 1300 also includes catheter sleeve 1302 including a plurality of pins 1312 protruding inward radially from the inner surface of catheter sleeve 1302 and evenly spaced about a circumference of the inner surface of catheter sleeve 1302. The example of steerable endoscopic system 1300 shown in FIG. 17 includes plurality of pins 1312 evenly spaced at 90 degrees about a circumference of the inner surface of catheter sleeve 1302. Plurality of pins 1312 is configured to complement and/or approximate plurality of slots 1310. Collar 1308 is configured to confront plurality of pins 1312 and consequently arrest translational movement of endoscope catheter 1304 proximally or distally relative to catheter sleeve 1302, except when plurality of pins 1312 is aligned with plurality of slots 1310. When plurality of pins 1312 is aligned with plurality of slots 1310, endoscope catheter 1304 may translate distally or proximally relative to catheter sleeve 1302 as plurality of pins 1312 pass through plurality of slots 1310. Because translation of endoscope catheter 1304 distally or proximally relative to catheter sleeve 1302 is only possible when plurality of pins 1312 is aligned with plurality of slots 1310, rotational visual orientation of endoscope catheter 1304 is maintained as steerable endoscopic system 1300 is steered and endoscope catheter 1304 translates proximally and distally.

Referring to FIG. 19, yet another example of a steerable endoscopic system 1400 is illustrated. Steerable endoscopic system 1400 includes endoscope catheter 1406, with outer surface 1404. Outer surface 1404 of endoscope catheter 1406 includes a plurality of collars 1408 protruding from outer surface 1404 and integral to endoscope catheter 1408 and evenly spaced apart longitudinally. Each collar of plurality of collars 1408 includes a plurality of slots, evenly spaced apart about a circumference of outer surface 1404. Steerable endoscopic system 1400 also includes catheter sleeve 1402. Catheter sleeve includes a plurality of pins about a circumference of the inner surface of catheter sleeve 1402. The plurality of pins is designed to complement each of the pluralities of slots in each of the plurality of collars 1408. When the plurality of pins is aligned with each plurality of slots in each of the plurality of collars 1408, endoscope catheter 1406 may translate distally or proximally relative to catheter sleeve 1402. In other examples of steerable endoscopic systems according to the present disclosure, in addition to a plurality of collars, a catheter sleeve may include a plurality of a plurality of pins, each plurality of pins about a circumference of the inner surface of the catheter sleeve and each plurality of pins evenly spaced apart longitudinally from each other plurality of pins. In still other examples of steerable endoscopic systems, a catheter sleeve may include a plurality of a plurality of pins while an endoscope catheter includes a single collar.

Referring to FIG. 20, a distal end view of yet another example of a steerable endoscope system 1500 is illustrated. Steerable endoscope system 1500 includes catheter sleeve 1502 and endoscope catheter 1506. Catheter sleeve 1502 includes a collar 1504 protruding inward from the inner surface of catheter sleeve 1502. Catheter sleeve 1502 includes a plurality of slots 1512 evenly spaced apart about the circumference of collar 1504 at 90 degrees. Endoscope catheter 1506 includes plurality of pins 1510 protruding outward from outer surface 1508 of endoscope catheter 1506 and evenly spaced about a circumference of outer surface 1508. Endoscope catheter 1506 includes plurality of pins 1510 evenly spaced at 90 degrees about a circumference of outer surface 1508 of endoscope catheter 1506. Plurality of pins 1510 is configured to complement and/or approximate plurality of slots 1512. Collar 1504 is configured to confront plurality of pins 1510 and consequently arrest translational movement of endoscope catheter 1506 proximally or distally relative to catheter sleeve 1502, except when plurality of pins 1510 is aligned with plurality of slots 1512. When plurality of pins 1510 is aligned with plurality of slots 1512, endoscope catheter 1506 may translate distally or proximally relative to catheter sleeve 1502 as plurality of pins 1510 pass through plurality of slots 1512. Because translation of endoscope catheter 1506 distally or proximally relative to catheter sleeve 1502 is only possible when plurality of pins 1510 is aligned with plurality of slots 1512, rotational visual orientation of endoscope catheter 1506 is maintained as steerable endoscopic system 1500 is steered and endoscope catheter 1506 translates proximally and distally. In other examples of steerable endoscopic systems according to the present disclosure, a catheter sleeve may include a plurality of collars evenly spaced apart longitudinally. In still other examples of steerable endoscopic systems according to the present disclosure, an endoscope catheter may include a plurality of a plurality of pins, even spaced apart longitudinally. In still other examples of steerable endoscopic systems according to the present disclosure, an endoscope catheter may include a plurality of a plurality of pins evenly spaced apart longitudinally on the outer surface of the endoscope catheter, and a catheter sleeve may include a plurality of collars evenly spaced apart longitudinally on the inner surface of the catheter sleeve.

Referring to FIG. 21, a perspective view of a distal end of yet another example of a steerable endoscope system 1600 with an example of a telescoping endoscope catheter 1605 including a keyed feature such as male chevron-shaped protrusions ("chevrons") 1601 added to endoscope catheter tip 1606 proximal to endoscope catheter tip 1606 is illustrated. Chevrons 1601 may be configured to aid with alignment of telescoping endoscope catheter 1605 about the longitudinal axis relative to pivot arm 1603 and catheter sleeve 1604. Shapes of chevrons 1601 may be configured to complement and/or approximate a shape of female chevron-shaped recesses 1602 added to pivot arm 1603 so as to aid with alignment of telescoping endoscope catheter 1605 about the longitudinal axis relative to pivot arm 1603 and catheter sleeve 1604. FIG. 22 illustrates a longitudinal cross-sectional view of steerable endoscope system 1600 with a cross-section taken along axis A-A.

Referring to FIG. 23, a perspective view of a distal end of yet another example of a steerable endoscope system 1700 with an example of a telescoping endoscope catheter 1705 including a keyed feature such as male chevron-shaped protrusions ("chevrons") 1701 seated in pivot arm 1703 and catheter sleeve 1704 is illustrated. Chevrons 1701 may be configured to aid with alignment by having a shape configured to complement and/or approximate a shape of female chevron-shaped recesses 1702 added to pivot arm 1703 so as to aid with alignment of telescoping endoscope catheter 1705 about the longitudinal axis relative to pivot arm 1703 and catheter sleeve 1704. FIG. 24 illustrates a longitudinal cross-sectional view of steerable endoscope system 1700 with a cross-section taken along axis B-B.

Referring to FIG. 25, a distal end view of yet another example of a steerable endoscope system 1800 with an example of a telescoping endoscope catheter 1803 with an elliptical longitudinal cross-sectional geometry is illustrated. FIG. 26 illustrates a side view of the distal end of steerable endoscope system 1800. Pivot arm 1801 may include an opening 1804 with an elliptical longitudinal cross-sectional geometry that is configured to have major and minor axes such that telescoping endoscope catheter 1803 may key into opening 1804 in pivot arm 1801 or the ability of telescoping endoscope catheter 1803 to rotate about the longitudinal axis relative to pivot arm 1801 may be at least limited. Catheter sleeve 1802 may include an elliptical longitudinal cross-sectional geometry that is configured to have major and minor axes such that the ability of telescoping endoscope catheter 1803 to rotate about the longitudinal axis relative to catheter sleeve 1802 may be at least limited. FIG. 27 illustrates a longitudinal cross-sectional view of steerable endoscope system 1800 with a cross-section taken along C-C.

Referring to FIG. 28, a distal end view of yet another example of a telescoping endoscope catheter 1900 is illustrated. Telescoping endoscope catheter 1900 may include keying features such as chevron-shaped protrusions ("chevrons") 1901 on the proximal end of distal catheter tip 1903 that may be configured to aid alignment of telescoping endoscope catheter 1903 relative to pivot arm 1801. FIG. 29 illustrates a perspective view of telescoping endoscope catheter 1900. FIG. 30 illustrates a top view of telescoping endoscope catheter 1900.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the disclosure may also relate, among others, to the following aspects:

A first aspect relates to a medical device, comprising: the elongate tube comprising a lumen extending therethrough, the elongate tube defining a longitudinal axis therethrough, the lumen comprising a surface with a first longitudinally-extending cross-sectional geometry; a movable member extending longitudinally at least partially within the lumen, the movable member comprising a second lumen extending therethrough, the movable member comprising an outer surface with a second longitudinally-extending cross-sectional geometry; and a camera extending longitudinally at least partially within the second lumen; and wherein the first longitudinally-extending cross-sectional geometry and the second longitudinally-extending cross-sectional geometry are configured to prevent the movable member from rotating about the longitudinal axis relative to the elongate tube as the movable member is translated distally or proximally.

A second aspect relates to the medical device of aspect 1, wherein the second longitudinally-extending cross-sectional geometry is configured to complement the first longitudinally-extending cross-sectional geometry of the surface of the lumen.

A third aspect relates to the medical device of aspect 1 or 2, wherein the second longitudinally-extending cross-sectional geometry is non-axisymmetric.

A fourth aspect relates to the medical device of any preceding aspect, wherein the first longitudinally-extending cross-sectional geometry is non-axisymmetric.

A fifth aspect relates to the medical device of aspect 1 or 2, wherein the second longitudinally-extending cross-sectional geometry is elliptical; and wherein the second longitudinally-extending cross-sectional geometry comprises a major axis and a minor axis, the major axis larger than the minor axis.

A sixth aspect relates to the medical device of aspect 5, wherein the first longitudinally-extending cross-sectional geometry is elliptical; wherein the first longitudinally-extending cross-sectional geometry comprises a second major axis and a second minor axis, the second major axis larger than the minor axis by the ratio; and wherein the first longitudinally-extending cross-sectional geometry is configured to complement the second longitudinally-extending cross-sectional geometry.

A seventh aspect relates to the medical device of aspect 5, wherein the first longitudinally-extending cross-sectional geometry is approximately circular; and wherein the elongate tube comprises attachments configured to complement the second longitudinally-extending cross-sectional geometry.

An eighth aspect relates to the medical device of aspect 1 or 2, wherein the second longitudinally-extending cross-sectional geometry comprises an oblong shape, a square shape, a detent, a groove, and/or a protruding feature.

A ninth aspect relates to the medical device of aspect 8, wherein the first longitudinally-extending cross-sectional geometry comprises an oblong shape, a square shape, a detent, a groove, a protruding feature, and/or an attachment configured to complement the second longitudinally-extending cross-sectional geometry.

A tenth aspect relates to the medical device of any preceding aspect, wherein the movable member comprises a shape set curve; wherein the elongate tube comprises a second shape set curve configured to complement the shape set curve; and wherein the shape set curve is configured to bias the orientation of the movable member in the elongate tube.

An eleventh aspect relates to a second medical device, comprising a third lumen, and the medical device of any preceding aspect housed in the third lumen, the third lumen defining a second longitudinal axis therethrough parallel to the longitudinal axis, wherein the medical device is configured to prevent the medical device from rotating about the second longitudinal axis relative to the third lumen as the medical device is translated distally or proximally relative to the third lumen.

A twelfth aspect relates to the medical device of any preceding aspect, wherein the elongate tube comprises a longitudinal slot connecting an outer elongate tube surface and the surface of the lumen; and wherein the medical device further comprises an outer clip, comprising: an outer clip body at least partially encircling a circumference of the outer elongate tube surface; and a pin protruding inward radially from the outer clip body and configured to protrude through the longitudinal slot and to complement a detent or groove in the second longitudinally-extending cross-sectional geometry.

A thirteenth aspect relates to the medical device of any preceding aspect, wherein the movable member comprises a member longitudinal slot connecting the outer surface and the second lumen, and an anchor connected to the camera and protruding outward through the member longitudinal slot; and wherein the anchor is configured to prevent the camera from rotating about an axis parallel to the longitudinal axis relative to the elongate tube and/or from translating distally and proximally beyond a longitudinal dimension of the member longitudinal slot.

A fourteenth aspect relates to the medical device of any preceding aspect, wherein the movable member comprises one or more additional lumens extending therethrough configured to house a deflection cable, a suction device, an irrigation device, an insufflation device, a camera lens washing device, or a light-emitting diode, or to pass accessories.

A fifteenth aspect relates to the medical device of any preceding aspect, wherein the surface of the lumen comprises a plurality of indents equally spaced apart about a circumference of the lumen; and wherein the outer surface of the movable member comprises a plurality of protrusions, each of which is configured to confront an indent of the plurality of indents.

In addition to the features mentioned in each of the independent aspects enumerated above, some examples may show, alone or in combination, the optional features mentioned in the dependent aspects and/or as disclosed in the description above and shown in the figures.

What is claimed is:

1. A medical device, comprising:
an elongate tube comprising a lumen extending therethrough, the elongate tube defining a longitudinal axis therethrough, the lumen comprising a surface with a first longitudinally-extending cross-sectional geometry;
a movable member extending longitudinally at least partially within the lumen, the movable member comprising a second lumen extending therethrough, the movable member comprising an outer surface with a second longitudinally-extending cross-sectional geometry; and
a camera extending longitudinally at least partially within the second lumen; and
wherein the first longitudinally-extending cross-sectional geometry and the second longitudinally-extending cross-sectional geometry are configured to prevent the movable member from rotating about the longitudinal axis relative to the elongate tube as the movable member is translated distally or proximally,
wherein at least one of the first longitudinally-extending cross-sectional geometry and the second longitudinally-extending cross-sectional geometry comprises a protruding feature, and
wherein the second lumen has a shape that at least partially complements a shape of the protruding feature.

2. The medical device of claim 1, wherein the second longitudinally-extending cross-sectional geometry is configured to complement the first longitudinally-extending cross-sectional geometry of the surface of the lumen.

3. The medical device of claim 1, wherein the second longitudinally-extending cross-sectional geometry is non-axisymmetric.

4. The medical device of claim 1, wherein the first longitudinally-extending cross-sectional geometry is non-axisymmetric.

5. The medical device of claim 1, wherein the first longitudinally-extending cross-sectional geometry comprises the protruding feature, and wherein the protruding feature is oriented in a radially inward direction.

6. The medical device of claim 5, wherein the second longitudinally-extending cross-sectional geometry comprises a groove configured to complement the protruding feature of the first longitudinally-extending cross-sectional geometry.

7. The medical device of claim 1, wherein the movable member comprises one or more additional lumens extending therethrough configured to house a deflection cable, a suction device, an irrigation device, an insufflation device, a camera lens washing device, or a light-emitting diode, or to pass accessories.

8. The medical device of claim 1, wherein the second lumen comprises a curved shape that partially follows a curvature of the protruding feature.

9. A medical device, comprising:
an elongate tube comprising a lumen extending therethrough, the elongate tube defining a longitudinal axis therethrough, the lumen comprising a surface with a first longitudinally-extending cross-sectional geometry;
a movable member extending longitudinally at least partially within the lumen, the movable member comprising a second lumen extending therethrough, the movable member comprising an outer surface with a second longitudinally-extending cross-sectional geometry; and
a camera extending longitudinally at least partially within the second lumen; and
wherein the first longitudinally-extending cross-sectional geometry and the second longitudinally-extending cross-sectional geometry are configured to prevent the movable member from rotating about the longitudinal axis relative to the elongate tube as the movable member is translated distally or proximally,
wherein the first longitudinally-extending cross-sectional geometry comprises a protruding feature, and wherein the protruding feature is oriented in a radially inward direction.

10. The medical device of claim 9, wherein the second longitudinally-extending cross-sectional geometry comprises a groove configured to complement the protruding feature of the first longitudinally-extending cross-sectional geometry.

11. The medical device of claim 9, wherein the second lumen has a shape that at least partially complements a shape of the protruding feature.

12. The medical device of claim 11, wherein the second lumen comprises a curved shape that partially follows a curvature of the protruding feature.

13. The medical device of claim 9, wherein the movable member comprises one or more additional lumens extending therethrough configured to house a deflection cable, a suction device, an irrigation device, an insufflation device, a camera lens washing device, or a light-emitting diode, or to pass accessories.

14. A medical device, comprising:
an elongate tube comprising a lumen extending therethrough, the elongate tube defining a longitudinal axis therethrough, the lumen comprising a surface with a first longitudinally-extending cross-sectional geometry;
a movable member extending longitudinally at least partially within the lumen, the movable member comprising a second lumen extending therethrough, the movable member comprising an outer surface with a second longitudinally-extending cross-sectional geometry; and a camera extending longitudinally at least partially within the second lumen; and wherein the first longitudinally-extending cross-sectional geometry and the second longitudinally-extending cross-sectional geometry are configured to prevent the movable member from rotating about the longitudinal axis relative to the elongate tube as the movable member is translated distally or proximally, wherein the first longitudinally-extending cross-sectional geometry comprises a protruding feature, and wherein the protruding feature is oriented in a radially inward direction, wherein the second longitudinally-extending cross-sectional geometry comprises a groove configured to complement the protruding feature of the first longitudinally-extending cross-sectional geometry, and wherein the second lumen has a shape that at least partially complements a shape of the protruding feature.

15. The medical device of claim 14, wherein the second lumen comprises a curved shape that partially follows a curvature of the protruding feature.

* * * * *